United States Patent
Fernfors et al.

(10) Patent No.: US 7,022,114 B2
(45) Date of Patent: Apr. 4, 2006

(54) ABSORBENT ARTICLE HAVING IMPROVED FIT AND ENHANCED ABSORPTION CAPACITY

(75) Inventors: Ingemar Fernfors, Mölndal (SE); Gerd Fihn, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 379 days.

(21) Appl. No.: 10/187,831

(22) Filed: Jul. 3, 2002

(65) Prior Publication Data

US 2003/0023213 A1     Jan. 30, 2003

Related U.S. Application Data

(60) Provisional application No. 60/302,668, filed on Jul. 5, 2001, provisional application No. 60/302,667, filed on Jul. 5, 2001, provisional application No. 60/302,669, filed on Jul. 5, 2001, provisional application No. 60/302,670, filed on Jul. 5, 2001.

(51) Int. Cl.
A61F 13/15        (2006.01)

(52) U.S. Cl. ............................ 604/385.201; 604/385.21

(58) Field of Classification Search ......... 604/385.101, 604/385.16, 385.201, 385.21, 378
See application file for complete search history.

(56) References Cited

U.S. PATENT DOCUMENTS

| | | | |
|---|---|---|---|
| 2,571,577 A | | 10/1951 | Howard |
| 3,890,973 A | | 6/1975 | Davis et al. |
| 4,685,915 A | * | 8/1987 | Hasse et al. ............... 604/378 |
| 4,701,178 A | | 10/1987 | Glaug et al. |
| 5,464,402 A | * | 11/1995 | Zajaczkowski ........ 604/385.21 |
| 5,788,686 A | | 8/1998 | Ahr et al. |
| 5,792,130 A | * | 8/1998 | Widlund et al. ....... 604/385.01 |
| 6,046,377 A | * | 4/2000 | Huntoon et al. ............ 604/368 |
| 6,162,959 A | | 12/2000 | O'Connor |
| 6,409,711 B1 | * | 6/2002 | Jonbrink ................ 604/385.01 |
| 6,425,890 B1 | | 7/2002 | Samuelsson et al. |
| 6,702,799 B1 | * | 3/2004 | Otsubo .................. 604/385.21 |

FOREIGN PATENT DOCUMENTS

| | | |
|---|---|---|
| SE | 507798 C2 | 7/1998 |
| SE | 515584 C2 | 9/2001 |
| WO | 95/07674 | 3/1995 |

\* cited by examiner

*Primary Examiner*—Tatyana Zalukaeva
*Assistant Examiner*—C Anderson
(74) *Attorney, Agent, or Firm*—Buchanan Ingersoll PC

(57) ABSTRACT

An absorbent article with a longitudinal direction and a transverse direction and including an absorption body enclosed in a cover, wherein the cover has a fluid-permeable surface and a fluid-impermeable surface and wherein the absorption body has at least one absorption layer, exhibiting a penetrating slit with a first cut edge and a second cut edge. The absorption layer is shaped by the material on both sides of the two cut edges being moved in a direction essentially at right angles to the slit and being locked in the moved position.

25 Claims, 14 Drawing Sheets

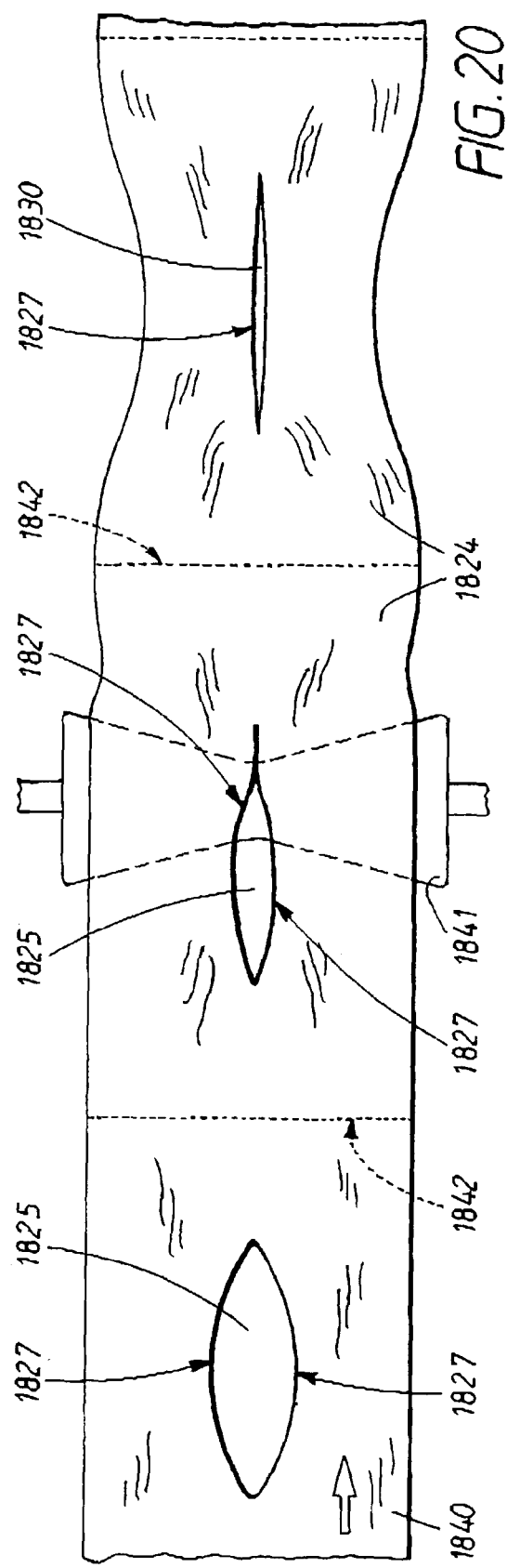
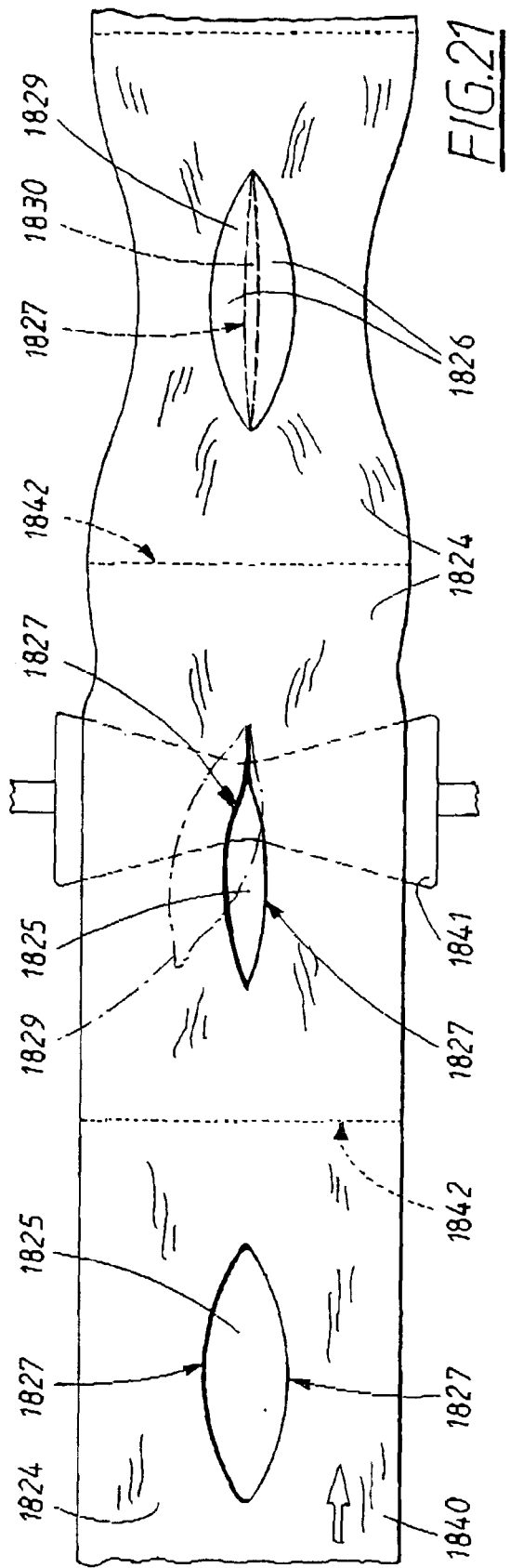

ABSORBENT ARTICLE HAVING IMPROVED FIT AND ENHANCED ABSORPTION CAPACITY

This application claims priority under 35 U.S.C. § 119 to U.S. Provisional Application Nos. 60/302,668, 60/302,667, 60/302,669, and 60/302,670 each application filed on 5 Jul. 2001, the entire contents of which are hereby incorporated herein by reference.

TECHNICAL FIELD

The invention pertains to an absorbent article with a longitudinal direction and a transverse direction and comprising an absorption body enclosed in a cover, the cover having a fluid-permeable surface and a fluid-impermeable surface, and the absorption body comprising at least one absorption layer, exhibiting a penetrating slit with a first cut edge and a second cut edge.

The invention also concerns a method of manufacturing the absorbent article.

BACKGROUND ART

Absorbent articles such as diapers, sanitary napkins and incontinence shields are intended to catch and absorb body fluids from a user's genital area. Depending on the application and the amount of fluid the article must be able to absorb, there are, of course, articles with different shapes and sizes. For instance, diapers for heavily incontinent adults are obviously considerably larger and have larger absorption capacity than diapers for infants. Furthermore, in addition to the demands for sufficient absorption capacity and leakage security, the articles are also required to be comfortable to wear. It is also important for adult users that the articles are discreet and able to be worn without being noticed under normal clothes.

The absorbent articles must thus be designed with sufficient absorption capacity in order to absorb the excreted body fluid, but still have a good fit so that they are comfortable and flexible to wear and so that they conform well to the user's body and prevent leakage. One difficulty in the shaping of an absorbent article intended to be worn in a user's crotch area is that the space between the user's legs is limited. This implies that the article, in order to be comfortable to wear, must be narrowest in the area where the greater part of the fluid released from the user is going to impact the article. Thus, there is an obvious risk that the area of the article that is wetted first is saturated with fluid and becomes incapable of absorbing further released fluid even though a large part of the absorbent material at the end portions of the article remains unused. This means that the risk of leakage is great even when the article has absorbed relatively small amounts of fluid. In order to prevent fluid leakage past the side edges of an absorbent article of this kind, it is therefore common to provide the article with some kind of edge barriers. Such edge barriers are often resilient and form raised physical barriers to the liquid flow. It is common to arrange elastic members, which are tightened around the user's legs, in diapers and incontinence shields of the kind worn as absorbent underpants, thereby keeping the edges of the article in sealing contact with the legs.

Resilient leg bands and raised barriers are usually, in articles such as diapers and incontinence shields for heavy incontinence, combined with the fact that the article is shaped with a relatively wide crotch portion in order to achieve sufficient absorption capacity within the wetting area of the article. Such a crotch area will be folded together between the user's legs during use, or will hang down between the legs as a fluid-collecting bag. Such shaping creates random channels which can give rise to leakage, is not particularly comfortable or discreet, and moreover functions poorly when the user is sitting down. For sanitary napkins and other absorbent articles where the demand for discretion during use is particularly great, such a clumsy and inelastic structure is not at all acceptable. Articles such as sanitary napkins and incontinence shields for light incontinence are also rather small and are not self-supporting, but are attached inside a pair of ordinary underpants, which during use holds the article in contact with the user's body. A structure with a depending or folded-together crotch area is thus not at all useful for this category of articles.

As is evident from the above, there is a need for an absorbent article that has a good fit, high leakage security and high absorption capacity in the initial wetting area, and that is discreet and comfortable to wear. It is also desirable to be able to offer an absorbent article, which has a fit so good that special forming elements or leakage barriers, for instance in the form of elastic members, can be avoided.

DISCLOSURE OF INVENTION

In the present invention an article has been achieved with a longitudinal direction and a transverse direction and comprising an absorption body enclosed in a cover, the cover having a fluid-permeable surface and a fluid impermeable surface, and the absorption body comprising at least one absorption layer exhibiting a penetrating slit with a first cut edge and a second cut edge, which article has a good fit, high leakage security, high absorption capacity, high discretion and comfort.

An article made in accordance with the invention is primarily characterized in that the two cut edges are displaced in relation to each other in such a manner that the absorption layer is shaped by the material on both sides of the two cut edges being moved in a direction essentially at right angles to the slit and being locked in the moved position.

By moving the material on both sides of the cut edges, a deformation of the absorption layer is brought about in a controlled manner. The deformation is a result of the stresses and strains which arise in the absorption layer when the cut edges are brought towards, or moved away from, one another and manifests itself in such a manner that the absorption layer is curved lengthwise (X-direction), breadthwise (Y-direction) and at right angles (Z-direction) to the plane of the absorption layer. When the material is moved inwards, an inward curving of the side edges of the absorption layer is moreover obtained if the slit is arranged in the longitudinal direction of the absorbent article. If the absorption layer already has inwardly curved edges before the movement of the cut edges, an increased curvature is obtained. Therefore, on the one hand, a shaping of the absorption layer in the plane, i.e. in the X-Y directions, is obtained, and, on the other hand, a shaping in space, i.e. in the Z-direction, at right angles to the X-Y directions, is obtained. As a result, the curved layer is extremely well suited as a component in an absorbent article, for example a diaper, a sanitary napkin, an incontinence shield or the like, as the curved shape can be made to follow the curvature of the user's body.

The slit in the absorption layer can be a simple cut or can be in the form of an opening, with a width which is different from zero. Such an opening in the absorption layer can be the result of a cutout part initially being removed from the absorption layer. The opening is suitably essentially boat-shaped or leaf-shaped, with pointed ends and a wider central portion. When the cut edges of such an opening are brought towards one another, the absorption layer can have a fluid-admission channel with a width which corresponds to the degree to which the cut edges are brought together. In an extreme case, the cut edges are brought together completely or made to overlap.

When the opening is formed by virtue of a cutout part having been removed from the absorption layer, the cutout part can be used in order to boost the absorption capacity in the shaped absorption layer. The cutout part can therefore be applied to the absorption layer, preferably placed over the fluid-admission channel, if one is present, on that side of the absorption layer which faces towards the user during use. Furthermore, the cutout part is preferably positioned symmetrically in relation to the centre line of the absorption layer, which extends in the longitudinal direction.

In another embodiment of the invention, the cutout part is applied below the absorption layer, on that side of the absorption layer which faces away from the user during use, symmetrically in relation to the centre line of the absorption layer, which extends in the longitudinal direction.

According to a preferred embodiment of the invention, a first area located along the first cut edge is arranged so that it overlaps a second area located along the second cut edge, the overlapping areas having at least one arcuate curved edge.

Due to the areas closest to the cut edges being made to overlap, with an overlap smallest at the ends of the slit and displaying a maximum between the ends, a curving of the absorption layer in the longitudinal direction perpendicular to the plane of the absorption layer, and a curving inwards of the side edges of the absorption layer are achieved. The longitudinal direction of the absorption layer here refers to the direction parallel to the slit in the absorption layer. Thus, on the one hand, a shaping of the absorption layer in the plane, i.e. in the X-Y directions, and, on the other hand, a shaping in the Z-direction, perpendicular to the X-Y directions are obtained.

According to an embodiment of the invention, the absorption layer has, in addition to the penetrating slit, an arcuate fold indication arranged symmetrically on each side of the slit, the arcuate fold indications being curved in a direction away from the slit, the absorption layer having a portion on each side of the slit, between the slit and the respective fold indication, which portion is folded along the fold indication, in a direction away from the slit.

The folded portions on both sides of the slit are preferably folded down completely against the absorption layer and can be fixed to the absorption layer in the folded-down position. Such fixation of the folded-down portions can, for instance, be achieved through gluing. It is also possible to use heat-meltable components in the absorption layer in order to attach the folded-down portions to the rest of the absorption layer. Another method for fixation of the folded-down portions to the absorption layer is to arrange a locking member over the folded-down portions. An example of such a locking member is a material layer that is attached, for example through gluing or welding, over the folded-down portions on both sides of the slit.

According to a preferred embodiment, the fold edges formed along the curved fold indications are brought together and fixed at a distance of 0–20 mm from each other. It may be suitable to retain a small gap between the folded edges. Such a gap can serve in the article as an admission channel for fluid and moreover constitute a temporary reservoir for fluid which has not yet had time to be absorbed by the absorption material in the article. The gap moreover promotes rapid spreading of fluid out into the end portions of the article.

By virtue of the curved fold edges being brought together, the absorption layer is given a curved, three-dimensional shape. As the absorption material in the folded-out portions on both sides of the slit is available for absorption of body fluid, it makes a contribution to the absorption capacity within the area around the slit without a depending "bag" being formed, or the absorption layer being folded together in an uncontrolled manner. The folded portions of the absorption layer also serve to reduce the width of the absorption layer on both sides of the slit. This can be used in the shaping of an anatomically adapted narrower crotch portion and makes it possible to obtain a three-dimensionally shaped absorption body with inwardly curved side edges on the basis of a plane, rectangular absorption blank.

The fixation of the absorption layer in the predetermined curved shape, preferably with the folded edges on both sides of the slit brought completely or partly together, is suitably brought about by a stabilizing means. Such stabilization is described in greater detail below.

According to the invention, it is also possible to form an absorption layer in which the areas on both sides of the slit are moved apart. Such an absorption layer is characterized in that the two cut edges are displaced in relation to one another in such a manner that the absorption layer has an opening with two terminal points and a length between the terminal points and with a width at right angles to the length, the width of the opening having a maximum between the terminal points, and also in that the absorption layer is curved in both the longitudinal direction and the transverse direction of the article, and in that the absorption layer is locked in the curved shape by stabilizing means.

By virtue of the cut edges of the slit being moved apart, an opening is formed in the absorption layer. At the same time, both a curving in the transverse direction and a curving in the longitudinal direction of the absorption layer at right angles to the plane of the absorption layer are brought about. In this connection, the longitudinal direction of the absorption layer means the direction parallel to the slit in the absorption layer, and the transverse direction of the absorption layer means the direction at right angles to the slit in the absorption layer. A shaping of the absorption layer out of the plane, i.e. in the Z-direction, at right angles to the X-Y directions is therefore obtained. As a result, the slit and curved layer is extremely well suited as a component in an absorbent article, for example a diaper, a sanitary napkin, an incontinence shield or the like. The curved shape can then be used in order to create a bowl shape on that side of the article which is intended to face the user during use. In such an embodiment, a curving in the longitudinal direction of the article following the body is also obtained. Alternatively, the article can be curved in the opposite direction, a raised portion being formed on the side which is intended to face the user during use. Such raised portions are above all suitable for creating direct contact between the body of the user and the absorbent article and are advantageously used on sanitary napkins.

The absorption layer is fixed in its curved state, with the slit widened to form a boat-shaped opening. Such fixation can be brought about, for example, by arranging a locking member over the opening, so that the portions immediately next to the respective cut edge on both sides of the opening are fixed at a predetermined distance from one another. An example of such a locking member is a material layer that is attached, for example through gluing or welding, over the absorption layer on both sides of the edges of the slit. Another way of locking the curved shape of the absorption layer is for the absorption layer to be shaped first, after which heat-meltable components in the absorption layer are used in order to bind the material, preferably fibres, in the absorption layer and thus fix the absorption layer in the curved shape.

According to an embodiment of the invention, the absorption layer exhibits at least a second slit, which is essentially parallel to the first slit and wherein each slit exhibits a first cut edge and a second cut edge, which are displaced in pairs in relation to each other in such a manner that the absorption layer exhibits at least one overlapping area along each slit wherein the overlapping areas along each slit have an arcuate curved edge.

In such an embodiment overlapping areas are formed at each slit, on each side of a straight line through the terminal points of each slit. Depending on the distance between the slits and the size of the overlapping areas, the overlapping areas along each slit may either be situated at a distance from each other, be contiguous to each other or overlap each other. The last-mentioned case occurs if the overlapping areas between the slits have a maximum width exceeding the distance between the slits. There will then be a portion between the slits consisting of three overlapping layers of the absorption layer. The parallel slits are preferably located at a mutual distance of 0.5–15 centimetres.

Absorbent articles of this kind generally exhibit two end portions and a crotch portion located between the end portions, where said crotch portion has a lesser extension in the transverse direction than the end portions. Thereby, it is especially advantageous if the slit is arranged at least mainly in the crotch portion. Furthermore, it is advantageous if the slit extends in the longitudinal direction of the article. When only one slit is made in the absorption layer, this is suitably arranged along the centre line of the article, which extends in the longitudinal direction. If two slits are made in the absorption layer, they are advantageously arranged symmetrically on each side of the centre line of the article, which extends in the longitudinal direction.

When the absorption layer has overlapping areas, these are suitably affixed to each other. Such fixation can, for instance, be achieved through gluing. It is also possible to use heat-meltable components in the absorption layer in order to attach overlapping parts of the absorption layer to one another, for example through heat binding or ultrasound welding. Another method for fixation of the overlapping areas to each other is by arranging a locking member over the overlapping portions. An example of such a locking member is a material layer that is attached, for example through gluing or welding, over the overlapping areas on both sides of the cut edges of the slit.

By bringing together and, if appropriate, overlapping the material at the sides of the slit, the absorption layer is given a curved, three-dimensional shape. As the absorption material in the areas that are arranged overlapping, or in a cutout part which has been arranged on the absorption layer, is available for absorption of body fluid, it makes a contribution to the absorption capacity within the area around the slit without a depending "bag" being formed, or the absorption layer being folded together in an uncontrolled manner. In the case of overlapping, the areas of the absorption layer, which are overlapped, also contribute to reducing the width of the absorption layer along the slit. This can be used in the shaping of an anatomically adapted narrower crotch portion in an absorbent article and makes it possible to obtain a three-dimensionally shaped absorption body with curved side edges on the basis of a plane, rectangular absorption blank. The invention can thus be said to offer a possibility for moving the absorption capacity, in a controlled manner, in the Z-direction, out of the X-Y-plane of the absorption material.

The fixation of the absorption layer in the predetermined curved shape is suitably accomplished by a stabilizing means.

Such a stabilizing means can, as earlier mentioned, be a stabilizing layer, which is firmly connected to the absorption layer, for example through gluing or welding.

The stabilizing layer can be arranged so that it also constitutes a distance layer between the absorption body and the fluid-permeable surface of the cover. A distance layer can perform several functions and can, for example, be a porous fluid reception layer, a fluid-transferring layer, a soft padding layer, a rewetting barrier, a camouflage layer, or perform two or several functions in combination.

A stabilizing layer can be arranged over one or both of the surfaces of the absorption layer and is thereby attached on both sides of the slit. If two stabilizing layers are used, the additional stabilizing layer can, for example, be a fluid-permeable cover layer or a fluid-impermeable cover layer, or a layer that, in a completed absorbent article, acts as a reinforcement layer, as a fluid reception layer, a fluid-dispersion layer or an additional absorption layer. If the absorption layer comprises overlapping areas, the stabilizing layer can be attached over the overlapping areas in the absorption layer, on either the same side as the overlapping areas, or the opposite side of the absorption layer.

The stabilizing means can also comprise a binding agent, which is part of the absorption layer, for example in the form of thermoplastic fibres or particles, such as fibres or particles of polyethene, polypropene, polyester, bicomponent fibres or the like. A combination of one or two stabilizing layers and a binding agent can also be used. Overlapping areas of the absorption layer can be affixed in an overlapping position by arranging an adhesive between the areas.

An additional method of locking the shape of the absorption layer is by using a stabilizing means in the form of a mechanical connection between overlapping areas. Such a mechanical connection can, for example, be accomplished through embossing, needling, or riveting of the overlapping areas.

The overlapping areas can comprise a part of the cover of the article. The overlapping areas can then comprise a part of a fluid-permeable cover layer forming part of the article, a part of a fluid-impermeable cover layer forming part of the article, or both parts. A fluid-permeable cover layer can also comprise a fluid-dispersion layer or a fluid reception layer. If the overlapping areas comprise a part of a fluid-impermeable cover layer, it is, in general, appropriate to see to it that the article still has a fluid-impermeable surface on that side of the article that is intended to be directed away from the user during use. Such fluid-impermeability can be accomplished through arranging a fluid-impermeable seal, for example, a fluid-impermeable weld, or a fluid-impermeable glue line between the overlapping areas. Alternatively, a fluid-impermeable material strip can be arranged over the joint between the overlapping areas.

A suitable absorption material for used in the absorption layer is a layer of dry-formed cellulose fluff pulp, for instance of the kind described in WO 94/10956 and with a density of 0.2–1.0 g/cm$^3$. Other suitable materials are highly compressed cellulose fluff pulp, with a density of the same order as that mentioned above, tissue layers, non-woven layers and absorbent foam materials. The absorption layer can comprise one or more layers of the same or different materials and advantageously also comprises superabsorbent materials, i.e. polymeric materials in the form of fibres, particles or the like with the ability to absorb body fluid many times their own weight, while forming a liquid-containing gel. The material layers in the absorption layer can be joined, for instance by gluing or welding, or mechanically, such as by embossing, needling or compression.

In order for an absorption material to be appropriate for slitting and forming in accordance with the invention, the material should have sufficient cohesion in order to be treated as a coherent layer. This can, for instance, be accomplished through admixture of a certain amount of binding agent, which is activated for cohesion of the absorption layer, to an absorbent fibre structure, such as a layer essentially consisting of cellulose fluff pulp. Examples of binding agents are thermoplastic fibres. Sufficient cohesion of an absorbent fibre structure can also be achieved through admixture of longer fibres and/or compression of the fibre structure. Other methods of accomplishing cohesion are by using supporting layers or reinforcement layers, such as net, non-woven layers or tissue layers, or through compression, embossing, needling or the like. Absorbent foam materials generally have sufficient cohesion ability of their own in order to be directly practicable in an absorption layer in accordance with the invention.

An absorbent article in accordance with the invention can be supplied with several slits surrounded by moved portions and arranged in the same or different material layers. For instance, an absorbent material layer can exhibit two slits arranged symmetrically on each side of a centre line extending in the longitudinal direction of the article. Furthermore, it is possible to imagine a slit that extends centrally in the longitudinal direction, and two or more slits arranged in the end portions of the article. When the material on both sides of the slit has been moved so far in the lateral direction that the absorption layer has overlapping areas, the curvature of the edges of the overlapping areas, as well as the maximum width of the overlapping areas, can be adjusted so that the shape conforms to the curvature of the user's body. For instance, it can be expedient that the curving in the longitudinal direction in the crotch portion of the article is greater than the curving in the longitudinal direction in the end portions.

In diapers for children it is suitable that the slit has a length of 15–40 centimetres, preferably about 25 centimetres, and the overlapping areas a maximum width of 2–10 centimetres, preferably about 6 centimetres. In diapers and other types of body-surrounding incontinence shields for adults it is suitable that the slit has a length of 20–60 centimetres, preferably about 30 centimetres, and the overlapping areas a maximum width of 2–14 centimetres, preferably about 8 centimetres. The length of the slit here refers to the distance between the two terminal points of the slit. The width of the overlapping areas refers to the distance between the cut edges, which are arranged overlapping. In sanitary napkins, or incontinence shields for light incontinence, the slit suitably has a length between the terminal points of 10–40 centimetres, preferably about 15 centimetres, and the overlapping areas a maximum width of 2–10 centimetres, preferably 5 centimetres.

The absorption layer can be formed from a plane and essentially rectangular blank, which after slitting and movement with any overlapping is given a three-dimensional curved hourglass-shape.

Thus, it is possible through the invention to accomplish an absorption body with a narrower crotch portion and wider end portions and with high absorption capacity in the crotch portion from an essentially plane and rectangular material layer. The absorbent article can be given a shape that conforms extremely well to the curvature of a user's crotch area. At the same time, the absorption material in any overlapping portions, in the form of an applied cutout part or in the form of moved material portions, on each side of the slit makes a predictable contribution, with regard to shape and capacity, to the absorption capacity in the crotch portion of the article.

However, it is not necessary that the absorption layer is rectangular from the outset. For instance, oval layers can be used, or layers that already from the outset have an hourglass-shape accentuated through slitting and folding of the absorption layer. It is also possible to use absorption layers which are hourglass-shaped from the outset and which are widened by the material on both sides of a slit in the absorption layer being moved apart and fixed in the moved-apart position.

For certain applications, it can be advantageous if the slit is somewhat displaced in a direction towards an end portion of the article. For instance, it can be expedient to arrange the slit closer to that end portion that during use is intended to be directed forwards on the user, as the wetting area in an absorbent article is in general situated somewhat ahead of the transverse centre line of the article. However, if shaping and/or additional absorption capacity is desired at the rear portion of the article, for example if the article is a sanitary napkin intended for night use, or a diaper or an incontinence shield which is to absorb loose faeces, the slit can be displaced somewhat rearwards on the article. Of course, it is possible, as mentioned earlier, to arrange two or more slits in the same article. Additional slits can then be arranged in the same layer as the first slit, or be placed in another, not necessarily absorbent, material layer. The slit in the absorption layer can also be used to form a raised portion conformed to the body. For instance, it is common that sanitary napkins are supplied with such raised portions, which should then be placed so that they can catch excreted body fluid as soon as it leaves the user's body. Another common function of such raised portions is the forming of a leakage seal rearwards, between the user's buttocks. Furthermore, the placement of one or more slits can be used to achieve diapers especially designed for boys or girls.

Absorbent articles such as sanitary napkins are often supplied with securing flaps, which are arranged on the side edges of the article and which during use are folded around the leg bands of the user's underpants and are secured on the outside of the underpants. Such securing flaps contribute to keeping the article extended between the leg bands of the underpants and constitute an additional protection against side edge leakage. Absorbent articles such as sanitary napkins and incontinence shields, according to the invention, can advantageously be supplied with securing flaps.

The invention also concerns a method for manufacturing an absorption layer for use in an absorbent article. In accordance with the invention, an absorption layer is supplied with at least one penetrating slit, through which a first cut edge and a second cut edge are formed. Thereafter, the slit absorption layer is led over a concave or a convex surface through which the cut edges are made to move at right angles to the longitudinal direction of the slit. When the shaping surface is concave, those areas of the absorption layer located on both sides of the slit are moved in a direction towards one another. With considerable movement, the absorption parts which are brought together can be made to overlap one another. In this connection, an overlapping area with at least one curved edge along the slit is formed. The concave surface can, for instance, be the surface of a concave roll, a concave fold sheet, or two conventional cylindrical rolls placed at an angle. By allowing the absorption layer to pass over the concave or convex surface with a certain pressure on the surface, the areas on each side of the slit will migrate towards, or away from, each other and gradually be brought over each other in an overlapping position, or be moved apart, depending on the shaping surface selected.

If the desired result is for parts of the absorption layer to be brought in over one another and to overlap one another, it is advantageous if the concave surface is supplied with a control element in the form of a peg or the like, which initiates movement of the cut edges of the slit and ensures that one of the areas is always brought in over the other area in the same way, i.e. that the areas are always assembled in the same order in relation to one another.

The absorption layer is preferably produced in a continuously running web, from which individual absorption layers are separated after the shaping.

In order to stabilize the three-dimensional shape formed after slitting and movement of the areas situated on both sides of the slit, the absorption layer can be bound to a stabilizing layer. The stabilizing layer is then suitably arranged over at least one surface on the absorption layer, across the extension direction of the slit. It is not required that the stabilizing layer is arranged along the entire length of the slit, but it may be sufficient to arrange a band across the slit.

Alternatively, the shape of the absorption layer can, after slitting and overlapping, be fixed through activation of a binding agent, which is part of the absorption layer. Such a binding agent can be thermoplastic fibres, the shape of the absorption layer being stabilized through heating and subsequent cooling of the absorption layer.

The slit or the slits in the absorption layer are preferably straight and essentially parallel to the longitudinal or transverse direction of the absorption layer. However, it is possible to use curved or crooked slits and/or oblique slits. The term slit here refers to principally one-dimensional cuts, or snips, as well as elongate openings.

BRIEF DESCRIPTION OF DRAWINGS

The invention will be described in greater detail below, with reference to the illustrative embodiments shown on the attached drawings, in which:

FIG. 20 shows a method of shaping an absorption layer according to the invention, FIG. 21 shows a method of shaping an absorption layer with application of a cutout part in connection with rolling according to the invention.

DESCRIPTION OF ILLUSTRATIVE EMBODIMENTS

Figure 1:
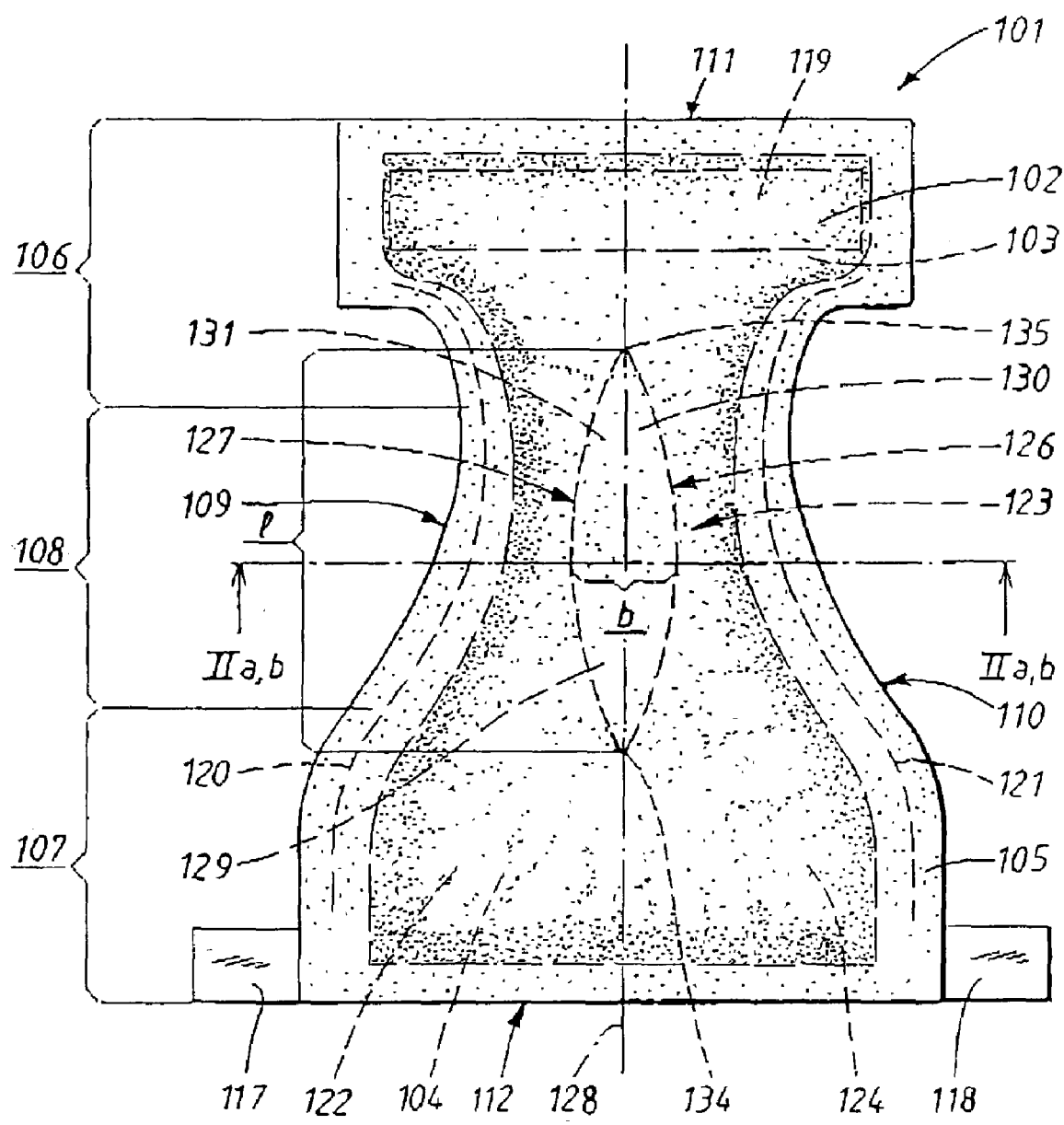
FIG. 1 shows a diaper according to the invention.
Figure 2A:
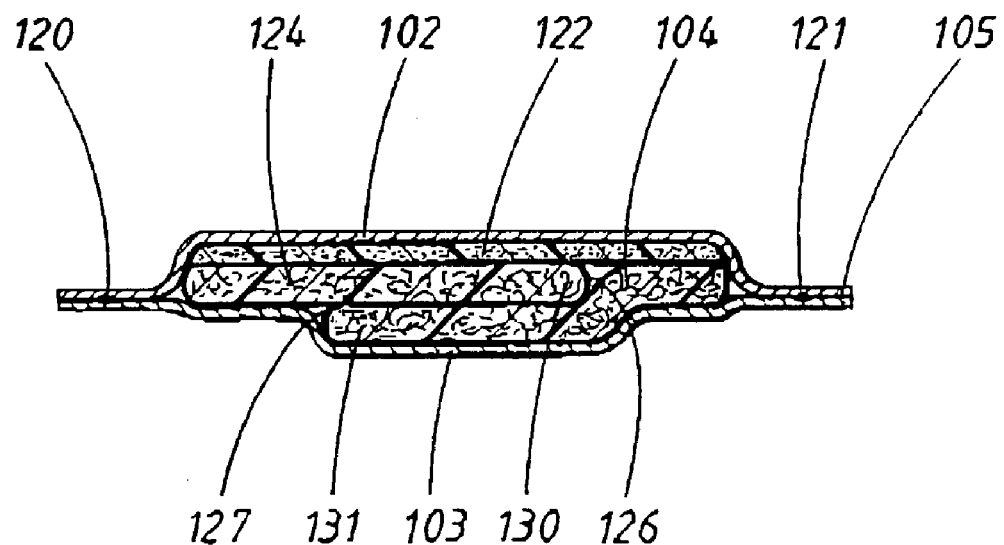
FIG. 2a shows a section along the line IIa—IIa through the diaper in FIG. 1 according to a first embodiment of the invention.
Figure 2B:
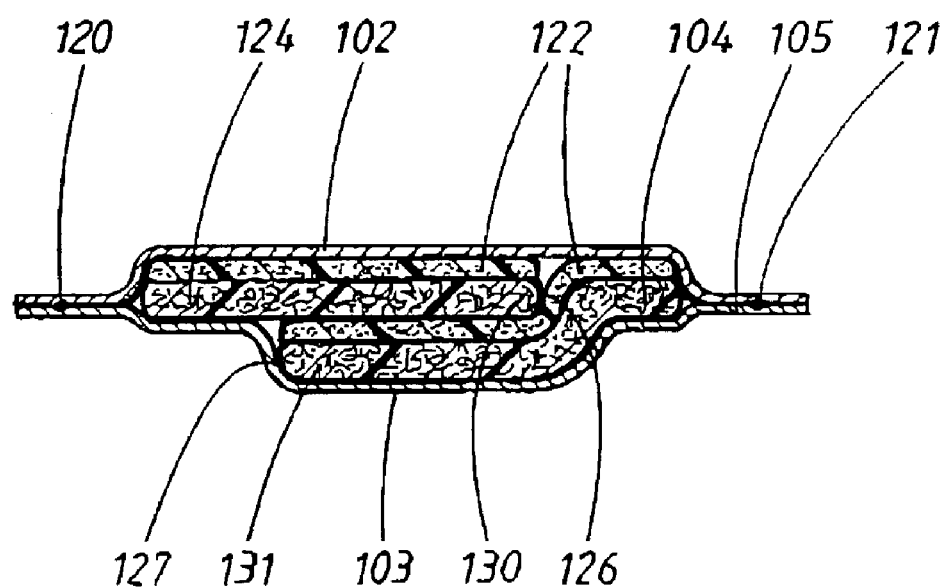
FIG. 2b shows a section along the line IIb—IIb through the diaper in FIG. 1 according to a second embodiment of the invention.

The diaper 101 shown in FIGS. 1, 2a and 2b comprises a first fluid-permeable cover layer 102, a second fluid-impermeable cover layer 103, and an absorption body 104 arranged between the cover layers 102, 103. The two cover layers 102, 103 have a larger extension in the plane than the absorption body 104 and project beyond the absorption body 104 around its entire periphery. The cover layers 102, 103 are bound to each other within the projecting portions 105, for instance by gluing or welding with heat or ultrasound.

The fluid-permeable cover layer 102 can consist of any material suitable for the purpose, such as layers of non-woven-material, perforated plastic film, net material, tow (parallel fibres) or the like. Of course, the cover layer 102 can also consist of a laminate of two or more layers of the same or different material. However, the fluid-permeable cover layer 102 does not have to be, within the scope of the invention, a separate component, but can be an integrated part of the absorption body 104. The projecting edge 105 around the absorption body 104 does not necessarily include the fluid-permeable cover layer 102 in such an embodiment. Examples of materials that can both be a cover layer 102 and be included in the absorption body 104 are foam, fibre wadding, non-woven material, or the like.

The fluid-impermeable cover layer 103 can consist of a fluid-impermeable plastic film, a non-woven layer, which has been covered with a fluid-blocking material, or some other flexible material layer, which has an ability to resist fluid penetration. However, it can be an advantage if the fluid-impermeable cover layer 103 exhibits certain breathability, i.e. allows passage of water vapour through the layer 103. The fluid-impermeable cover layer 103 can, like the fluid-permeable cover layer 102, be an integrated part of the absorption body and may, for instance, consist of a fluid-impermeable skin-resembling surface on an absorbent foam material.

The diaper 101 has an elongate form, with wider front and rear portions 106,107 and a narrower, intermediate crotch portion 108. The front portion 106 is the part of the diaper 101 that is intended to be directed forwards on the user, when the diaper is used, and the rear portion 107 is the part of the diaper that is directed rearwards on the user. In addition, the diaper 101 has two longitudinal, side edges 109, 110, which are curved inward, a front edge 111 and a rear edge 112.

The diaper 101 is of the type that during use is secured together, so that it, in a pants-resembling manner, encloses the lower part of the user's torso. For this purpose a tape flap 117, 118 is arranged projecting from each side edge 109, 110 adjacent to the rear edge 112 of the diaper. The tape flaps 117, 118 are intended to cooperate with a receiving area 119 arranged on the fluid-impermeable cover layer 103 on the front portion 106 of the diaper 101. Such a receiving area 119 suitably involves some form of reinforcement of the fluid-impermeable cover layer 103, for example in the form of an additional plastic layer or a coating arranged on the fluid-impermeable cover layer 103. Of course, it is alternatively possible to imagine other types of securing arrangements for the diaper 101, such as buttons and buttonholes, hooks and eyes, press studs, hook-and-loop fasteners or the like. A further alternative is that the diaper is a so-called pant diaper, which means that it is supplied to the user as a continuous absorbent pair of pants. Another common type of diaper is secured by a belt in which the diaper is firmly or removably suspended.

Furthermore, the diaper 101 is provided with pretensionally arranged, longitudinal, elastic members 120, 121, arranged along the side edges 109, 110 of the diaper. The elastic members 120, 121 contribute during use to curving of the diaper 101 along the user's body and constitute at the same time the leg elastic of the diaper. Thus, the elastic members 120, 121 serve to keep the side edges 109, 110 of the diaper in sealing contact with the user's legs, in order to counteract the emergence during use of gaps between the diaper and the user's body, through which body fluid can leak out of the diaper. The elastic members are not necessary to the invention, and so can be excluded, since an absorption body 104 in accordance with the invention has a very good fit and conforms well to the user's body, even without elastic members 120, 121.

The absorption body 104 can be made up of one or more layers of absorbent material, such as cellulose fluff pulp, tissue, absorbent foam, etc. It is also common that the absorption body comprises superabsorbents, i.e. polymeric materials that can absorb body fluid many times their own weight while forming a hydrogel. Such superabsorbents exist generally in the form of particles, but also fibres, flakes, granulates and film are to be found. In addition, the absorption body 104 can comprise non-absorbent components such as stiffening elements, forming elements, binding agents, etc. Different types of fluid-receiving porous structures such as fibre waddings or the like can also be included in the diaper 101.

The absorption body 104 comprises, in accordance with the invention, an absorption layer 124, which essentially has the same shape in the X-Y plane as the two cover layers 102, 103. The absorption layer 124 is suitably formed from a layer material with good cohesion, for instance the dry-formed cellulose fluff material that is described in WO 94/10956. Other suitable materials are highly compressed cellulose fluff pulp, tissue layer, non-woven layer and absorbent foam material. Absorbent fibre materials should have a density of 0.2–1.0 g/cm$^3$, with regard to the fibrous structure.

In the absorption layer 124, a cut in the form of a slit with a first and a second cut edge 126, 127 is arranged. The slit is essentially parallel to the longitudinal direction of the diaper 101 and is essentially arranged in the crotch portion 108. The slit has two terminal points 134, 135 and a length, l, between the terminal points 134, 135. The cut edges 126, 127 of the slit are brought to overlap around the centre line 128 of the diaper extending in the longitudinal direction, so that the crotch portion 108 of the diaper 101 exhibits an area 129 with double layers of the absorption layer 124. A first area 130 of the absorption layer 124, situated between the first cut edge 126 and the first side edge 109, is brought in over the absorption layer 124, in a direction away from the longitudinal centre line 128, and a second area 131 of the absorption layer 124 between the second cut edge 127 and the second side edge 110 is brought in the opposite direction in over the absorption layer 124. The overlapping of the areas 130, 131 of the absorption layer 124, which are situated on each side of the slit, is performed in such a manner that the cut edges 126, 127 are curved to an arcuate form. This implies that the overlapping and therewith the width, b, of the overlapping area 129 is greatest between the terminal points 134, 135 of the slit and decreases to zero in a direction towards the terminal points. In the shown embodiment, the overlapping area 129 is symmetrical in the longitudinal direction as well as in the transverse direction. Although this is a preferred embodiment, other embodiments are possible within the scope of the invention. For instance, it is not required that the overlapping area 129 has its width maximum at the centre point of the slit. Thus, the width, b, can be greatest closer to one of the terminal points 134, 135 of the slit.

Furthermore, the diaper 101 comprises a fluid-transferring layer 122. FIGS. 2a and 2b show different embodiments of the diaper 101 in FIG. 1. In the embodiment shown in FIG. 2a the entire fluid-transferring layer 122 is arranged between the fluid-permeable cover layer 102 and the absorption layer 124. In FIG. 2b the fluid-transferring layer 122 is slit together with the absorption layer 124 and is overlapped in the same manner as the absorption layer 124 at the crotch portion 108 of the diaper 101.

In the shown embodiments the fluid-transferring layer 122 has the same shape and size in the plane as the absorption layer 124, which, of course, is not necessary to the invention. Thus, the fluid-transferring layer 122 can be smaller or larger than the absorption layer 124 and have a different shape to the absorption layer 124.

The fluid-transferring layer 122 suitably has a higher porosity than the absorption layer 124 and has a good ability to receive and distribute fluid over the absorption layer 124, and an ability to release fluid to the absorption layer. The fluid-transferring layer 122 also forms a distance layer between the fluid absorbed in the absorption layer 124 and the user's body and thereby reduces or prevents rewetting, i.e. that already absorbed body fluid penetrates back out through the fluid-permeable cover layer 102. In general, it is an advantage if the fluid-transferring layer 122 comprises a thermoplastic component, which can be used to bind the fluid-transferring layer 122 together with the fluid-permeable cover layer 102 and/or the absorption layer 124. Thus, the fluid-transferring layer 122 can be bound together with the absorption layer 124 and in this manner serve as stabilizing means in order to keep the absorption layer 124 in the overlapping, three-dimensionally shaped state.

In the embodiment shown in FIG. 2b, where the fluid-transferring layer 122 extends in between the overlapping portions 130, 131 of the absorption layer 124, the fluid-transferring layer 122 also constitutes a transport channel into the absorption body 104 as fluid can rapidly reach in between the overlapping areas of the absorption layer 124.

The fact that the absorption layer 124 is slit and the areas 130, 131 situated on each side of the slit are brought to overlap, as described in the above, results in the diaper 101 being given a curved shape fitted to the body in the crotch portion 108, and also additional absorption capacity being supplied in the crotch portion 108. Thus, a thicker, more absorbent portion is obtained in a controlled manner in the area of the diaper 101 that is expected to be wetted first by body fluid and, at the same time, the crotch portion 108 can be made considerably narrower than is possible with conventional diapers. The additional amount of absorption material is localized to a small, relatively narrow area of the crotch portion 108, which makes the diaper comfortable to wear despite the increased absorption capacity. Within the overlapping portion 129, a stabilization and a stiffening of the crotch portion 108 is also obtained.

Such stiffening counteracts an uncontrolled deformation and fold formation, something that also contributes to enhanced comfort, and to the fact that the diaper 101 is discreet to wear and safe against leakage.

As earlier implied, it is suitable to lock the three-dimensional shape of the absorption layer 124 in some way. For instance, the absorption layer can be bound with at least one stabilizing layer, such as a cover layer 102, 103, a fluid transferring layer 122, or some other material layer forming part of the diaper. The binding can be performed in any suitable way, for instance through gluing, needling or welding. It is also possible to stabilize the three-dimensional shape of the absorption layer 124 through activation of a binding agent forming part of the layer 124, for instance thermoplastic fibres or particles, or through needling of the overlapping area 129.

Figure 3:
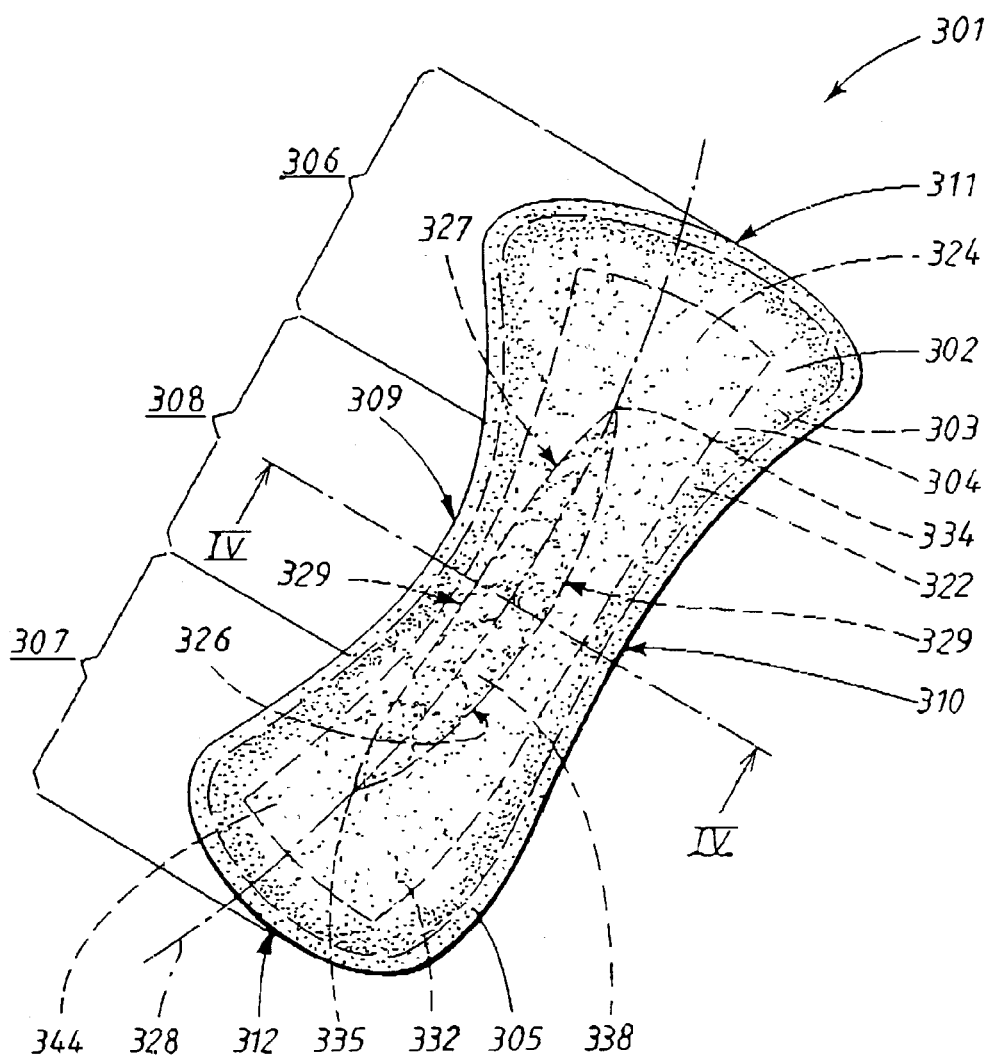
FIG. 3 shows an incontinence shield according to the invention.

The incontinence shield 301 shown in FIG. 3 has the same fundamental construction as the diaper in FIGS. 1 and 2a, b and thus comprises a first fluid-permeable cover layer 302, a second fluid-impermeable cover layer 303, and an absorption body 304 arranged between the cover layers 302, 303. The two cover layers 302, 303 have a larger extension in the plane than the absorption body 304 and form a projecting cover edge 305 around the entire periphery of the absorption body 304. The cover layers 302, 303 are bound to each other within the projecting cover edge 305, for example by gluing or welding with heat or ultrasound. The materials used in the different components in the incontinence shield 301 can be chosen the same way as for the diaper shown in FIGS. 1 and 2a, b.

The incontinence shield 301 is generally hourglass-shaped, with wider end portions 306, 307 and a narrower intermediate crotch portion 308. Furthermore, the incontinence shield 301 has two essentially longitudinal, inwardly curved side edges 309, 310 and two essentially transverse end edges 311, 312.

The incontinence shield 301 is of the type intended to be worn inside a user's underpants and is supplied, for this purpose, with a securing means 332, in the form of a rectangular, longitudinal area of self-adhesive glue. The embodiment of the securing means 332 shown is only intended as an example. Thus, it is possible to use other forms of adhesive securing means, for example other patterns, or locations of the securing means. Also other types of securing means, such as friction linings, mechanical securing means such as hook-and-loop linings, clips, press studs, securing flaps, or the like, can be used individually or in combination with adhesive securing means or with each other. Adhesive securing means 332 are usually protected before use with some type of detachable protective sheet, for instance a silicone-treated paper sheet, or the like.

To give the incontinence shield 301 a curved shape in the longitudinal direction and in a controlled manner shape a narrow crotch portion 308 with curved side edges 309, 310 and at the same time supply sufficient absorption capacity at the crotch portion 308, a cut in the form of a slit with two cut edges 326, 327 is arranged in an absorption layer 324, after which an overlapping, boat-shaped area 329 is formed along the slit. An area 330, 331, on each side of the slit and situated between a cut edge 326, 327 of the slit and a corresponding side edge 309, 310 of the incontinence shield 301, has been brought to overlap, as has been described in connection with the diaper 301 shown in FIGS. 1 and 2a, b.

Figure 4:
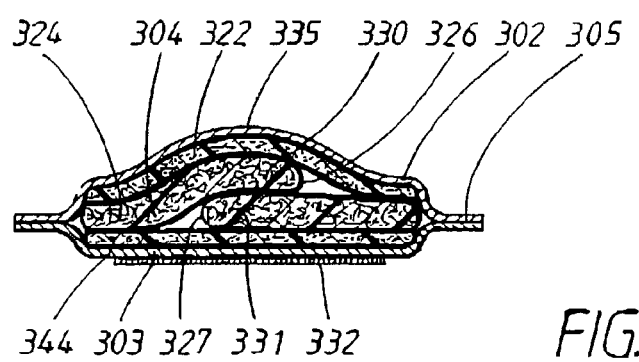
FIG. 4 shows a section along the line IV—IV through the incontinence shield in FIG. 3.

As shown in FIG. 4, the overlapping is performed so that an essentially plane surface is formed at the fluid-permeable cover layer 303 and so that a raised portion 338 is formed on that side of the incontinence shield that during use is intended to be directed towards the user. Of course, it is alternatively possible to allow the overlapping area 329 to bulge at that surface that during use is intended to be directed away the user. In such an embodiment the absorption layer 324 rather forms a bowl shape at the fluid-permeable cover layer 302. Intermediate shapes, where the overlapping area 329 somewhat bulges at both the fluid-permeable cover layer 302 and the fluid-impermeable cover layer 303, are also conceivable.

An incontinence shield 301 is held during use in close contact with the user's body owing to the pressure of the user's underpants. To prevent the user from being aware of the surface of the incontinence shield 301 through the fluid-permeable cover layer 302 as feeling irregular and uncomfortable, due to the presence of the overlapping area 329 in the absorption body 304, a distance layer 322 is arranged between the fluid-permeable cover layer 302 and the absorption body 304. Such a distance layer 322 can, as earlier mentioned, perform several functions. For instance, it is common, above all in incontinence shields and diapers, to arrange porous, usually resilient material layers as fluid-receiving layers with high momentary fluid-absorbing ability. Furthermore, the layer 322 can serve as a fluid-dispersing and fluid-transferring member between the fluid-receiving surface in an absorbent article and the absorption body of the article. The distance layer 322 can consist of a single or of several layers, for example with different compositions and/or different functions from each other. Examples of materials commonly used in distance layers are polyester waddings, bulky non-woven materials, different types of laminates, crosslinked cellulose fibres or the like. A distance layer should preferably be less hydrophilic and have higher porosity than the absorption layer lying inside it and should be soft and pleasant against the user's body.

The absorption body 304 comprises further, in the shown embodiment, a storage layer 344, which is placed between the absorption layer 324 and the fluid-impermeable cover layer 303. The storage layer 344 suitably has good fluid-dispersing ability and can absorb and store fluid that has been transferred from the absorption layer 324. Also the storage layer 344 can be used as a stabilizing layer and thus be bound to the absorption layer 324.

Figure 5:
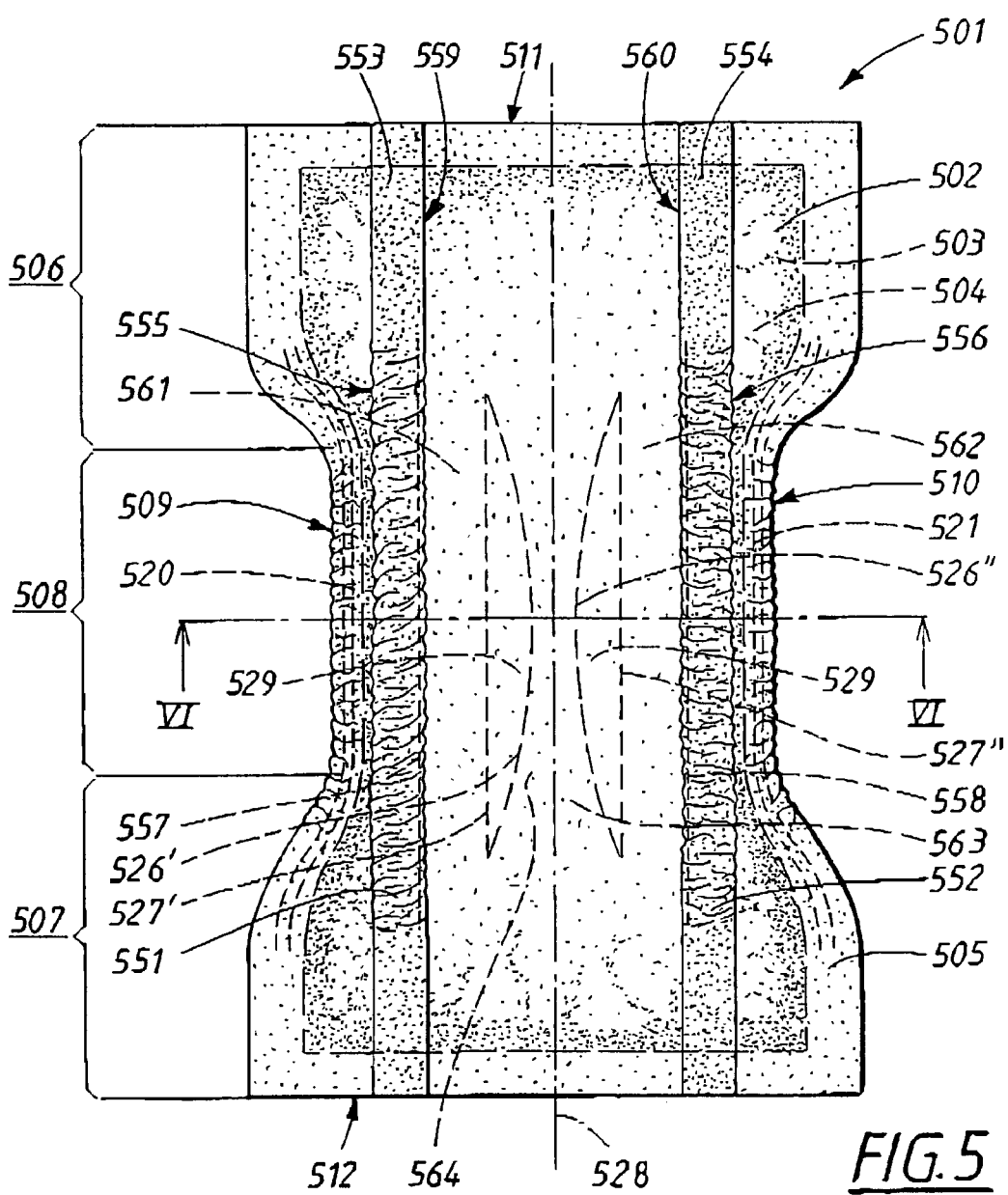
FIG. 5 shows a diaper according to a further embodiment of the invention.
Figure 6:
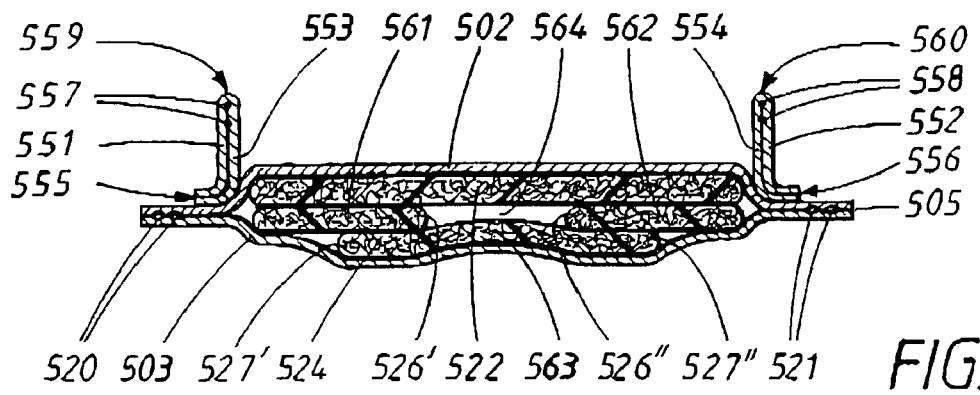
FIG. 6 shows a section along the line VI—VI through the diaper in FIG. 5.

FIGS. 5 and 6 show another diaper 501 according to the invention. The diaper 501 is essentially constructed the same way as the diaper in FIGS. 1 and 2a, b. Thus, the diaper in FIGS. 5 and 6 comprises a fluid-permeable cover layer 502, a fluid-impermeable cover layer 503, and an absorption body 504 arranged between the cover layers 502, 503. The cover layers 502, 503 are bound to each other within a projecting cover edge 505 around the absorption body 504.

The diaper 501 is principally hourglass-shaped, with wider end portions 506, 507 and a narrower, intermediate crotch portion 508. Furthermore, the diaper 501 has two longitudinal, inwardly bent side edges 509, 510 and two end edges 511, 512.

The diaper 501 is provided with pretensionally arranged, longitudinal, elastic members 520, 521, arranged along the side edges 509, 510 of the diaper. The elastic members 520, 521 contribute during use to curving of the diaper 501 along the user's body. Thus, the elastic members 520, 521 serve to keep the side edges 509, 510 of the diaper in contact with the user's legs. The elastic members are not necessary to the invention, and so can be excluded, since an absorption body 504 according to the invention has a very good fit and conforms well to the user's body, even without elastic members 520, 521. Moreover, the diaper 501 has inner elastic barriers 551, 552. The inner elastic barriers 551, 552 consist of double folded material strips 553, 554. The material strips 553, 554 suitably consist of material capable of resisting fluid penetration, for instance hydrophobic non-woven, plastic film or laminate of non-woven and plastic film. Each material strip 553, 554 is secured to the fluid-permeable cover layer 502 along an attachment edge 555, 556 and comprises pretensionally arranged elastic members 557, 558 at an opposite fold edge 559, 560.

In FIG. 5 the inner barriers 551, 552 are shown with the elastic members 557, 558 extended. The barriers 551, 552 are then lying down towards the fluid-permeable cover layer 502. To ensure that the barriers, during use, form fluid-catching side pockets along the side edges 509, 510 of the diaper 501, the double folded material strips 553, 554 are secured down to the fluid-permeable cover layer 502 adjacent to the end edges 511, 512 of the diaper 501. When the diaper is used, the elastic members 557, 558 are contracted and the inner barriers 551, 552 then adopt the raised shape shown in FIG. 6. The elastic members 557, 558 in the inner barriers 551, 552 cooperate with the elastic members 520, 521 in the projecting cover edge 505 at the side edges 509, 510 of the diaper.

The diaper 501 is shown without fastening members and can, in the shown shape, be used as an insert in a pair of panties or in special pant diapers, tie-pants or the like. Alternatively, the diaper can be supplied with fastening members, for instance of the kind described in connection with the diaper shown in FIGS. 1 and 2a, b. Also other types of fastening members known for the purpose, such as hook-and-loop surfaces, button/buttonhole, belt or the like can be used. It is also possible to imagine that the diaper is delivered constructed as an absorbent pant diaper.

The absorption body 504 comprises an absorption layer 524, in which two cuts in the form of slits are arranged, each with a first and a second cut edge 526', 527'; 526", 527". The slits are essentially parallel to the longitudinal direction of the diaper 501 and are essentially arranged in the crotch portion 508, symmetrically on each side of the longitudinal centre line 528 of the diaper 501. The cut edges 526', 527'; 526", 527" of the slits are brought to overlap in such a manner that an area 561, 562 along each side edge 509, 510 of the diaper 501 is brought in towards the longitudinal centre line 528 of the diaper, above an area 563 of the absorption layer 524 centrally situated between the slits. "Above" here means that the absorption areas 561, 562 at the side edges 509, 510 are arranged closer to the fluid-permeable cover layer 502 than the absorption area 563 centrally situated between the slits is. Through this arrangement a cavity 564 is formed between the cut edges 526', 527' situated most closely to the longitudinal centre line 528. This cavity 564 has the shape of a channel extending in the longitudinal direction of the diaper, which channel during use serves to temporarily retain fluid and to disperse the fluid in the longitudinal direction of the diaper. The cavity 564 can, if so wished, be filled with, for example, fibre waddings, a foam material, or any other material with good fluid-transporting properties.

Furthermore, the diaper 501 comprises a fluid-transferring layer 522. In the shown embodiment the entire fluid-transferring layer 522 is arranged between the fluid-permeable cover layer 502 and the absorption layer 524. Alternatively, the fluid-transferring layer 522 can be slit together with the absorption layer 524 and may be included in the overlapping at the crotch portion 508.

Instead of arranging the area 564, centrally situated between the slits, below the areas 561, 562 closest to the side edges 509, 510, as shown in FIG. 6, it is of course possible to use the reverse arrangement, where the central area 564 is arranged above the side areas 561, 562.

Figure 7:
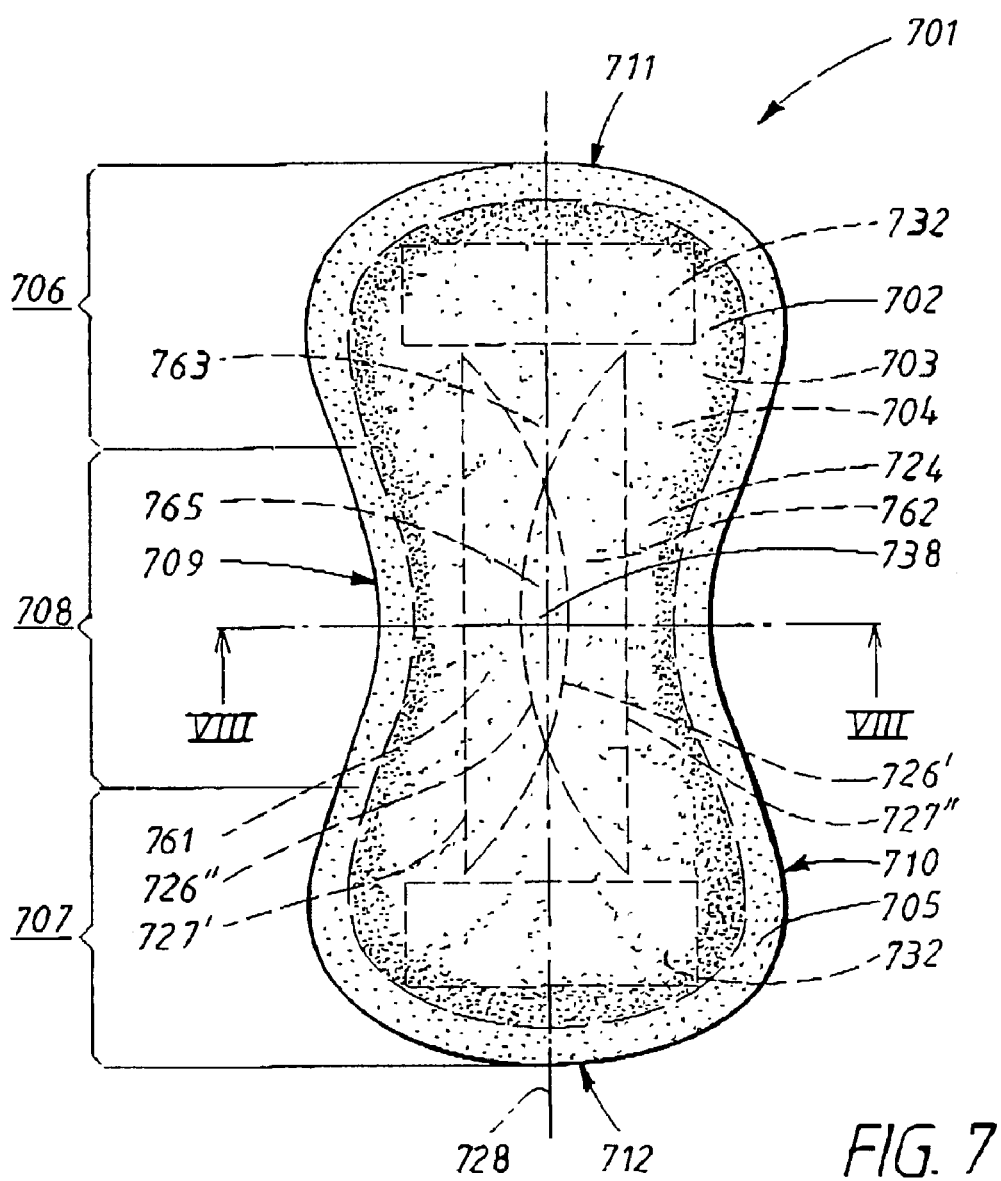
FIG. 7 shows a sanitary napkin according to the invention.
Figure 8:
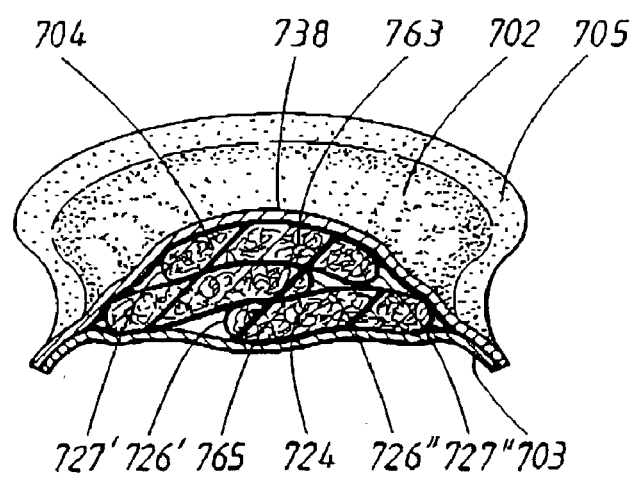
FIG. 8 shows a section along the line VIII—VIII through the sanitary napkin in FIG. 7.

The sanitary napkin 701 shown in FIGS. 7 and 8 comprises a fluid-permeable cover layer 702, a fluid-impermeable cover layer 703, and an absorption body 704 arranged between the cover layers 702, 703. The two cover layers 702, 703 have a larger extension in the plane than the absorption body 704 and form a projecting cover edge 705 around the entire periphery of the absorption body 704. The cover layers 702, 703 are bound to each other within the projecting cover edge 705, for example by gluing or welding with heat or ultrasound. The materials used in the different components in the sanitary napkin 701 may be chosen the same way as for the embodiments described above.

The sanitary napkin 701 is principally hourglass-shaped, with wider end portions 706, 707 and a narrower, intermediate crotch portion 708. Furthermore, the sanitary napkin 701 has two principally longitudinal, inwardly curved side edges 709, 710 and two principally transverse end edges 711, 712.

The sanitary napkin 701 is intended to be worn inside a user's underpants and is supplied with securing means 732 in the form of rectangular areas of self-adhesive glue arranged in the transverse direction of the sanitary napkin 701, at each end portion 706, 707. As mentioned earlier, a number of different types and shapings of securing means can be used to secure an absorbent article inside a pair of underpants.

The absorption body 704 comprises an absorption layer 724, in which two cuts in the form of slits are arranged, each with a first and a second cut edge 726', 727'; 726", 727". The slits are essentially parallel to the longitudinal direction of the sanitary napkin 701 and are essentially arranged in the crotch portion 708, symmetrically on each side of the longitudinal centre line 728 of the sanitary napkin 701. The cut edges 726', 727'; 726", 727" of the slits are brought to overlap in such a manner that a side area 761, 762 along each side edge 709, 710 of the sanitary napkin 701 is brought in towards the longitudinal centre line 728 of the sanitary napkin, with the first cut edges 726', 726" brought beyond each other so that a boat-shaped area, which is laid in overlap, is formed along the longitudinal centre line 728.

The overlapped area 765 formed by the side areas 761, 762 is in the shown example arranged below an area 763 of the absorption layer 724 centrally situated between the slits. "Below" is here intended to mean that the absorption areas 761, 762 at the side edges 709, 710 are arranged closer to the fluid-impermeable cover layer 702 in relation to the absorption area 763 centrally situated between the slits.

Due to the side areas 761, 762 of the absorption layer 724 being brought to overlap below the area 763 of the absorption layer 724, centrally situated between the slits, a central area with three layers of the absorption layer 724 is formed. In this manner, a well-defined raised portion 738 centrally extending along the longitudinal centre line 728 has been accomplished, which raised portion gives a shape which is anatomically well-adapted for female users. The raised portion 738 is during use in contact with the user's vaginal opening and can thus catch menstrual fluid as soon as it leaves the user's body. The excreted fluid can be absorbed by the built-up absorption material in the crotch portion 708.

The cross-section shown in FIG. 8 of the sanitary napkin in FIG. 7 shows how the portions of the sanitary napkin 701, situated beyond the cut, are curved out of the plane of the sanitary napkin 701. The curving arises as a result of the slitting and the overlapping of the material areas situated along the slits. The extent of the curving is controlled by the number of slits, the length of the slit or the slits, and by how large the overlapping is. By overlapping parts of the absorption layer 724, as earlier mentioned, both a curving of the side edges 709, 710 in a direction towards the longitudinal centre line and a curving in the longitudinal and transverse direction are obtained, out of the plane of the sanitary napkin.

The absorption body 704 in the sanitary napkin shown in FIGS. 7 and 8 consists of a single absorption layer 724. Of course, further layers and components can, however, be part of the absorption body 704, as has been specified in connection with the embodiments earlier described. The slit absorption layer 724 is suitably locked in the overlapped and curved state through being welded or glued to one or both of the cover layers 702, 703. Alternatively, or in combination therewith, the overlapping portions can be bound together by some binding agent. Such a binding agent can be arranged solely between the overlapping portions, or consist of a thermoplastic component in the absorption body. Suitable thermoplastic binding agents that can be mixed with the absorption material in the absorption layer 724 are thermoplastic fibres, which are activated through heating and compression or welding. Of course, it is also possible to use a separate locking means, for example a stabilizing layer, in order to keep the absorption layer 724 in the overlapped state.

Also the absorbent articles shown in FIGS. 1–6 are curved in the longitudinal as well as in the transverse direction due to the slitting and the overlapping of the absorption layers, which are part of the article. As it is possible to choose whether the crotch portion of the articles is going to be bowl-shaped or supplied with a raised portion at the fluid-permeable surface on the article, the transverse curving has not been shown in the sections in FIGS. 2a, b and 6. Furthermore, the portions of the articles situated beyond the cut are not shown in FIGS. 2a, b and 6. However, it is obvious that also these articles are curved in the longitudinal direction correspondingly to the sanitary napkin 701 shown in the FIGS. 7 and 8.

Figure 9:
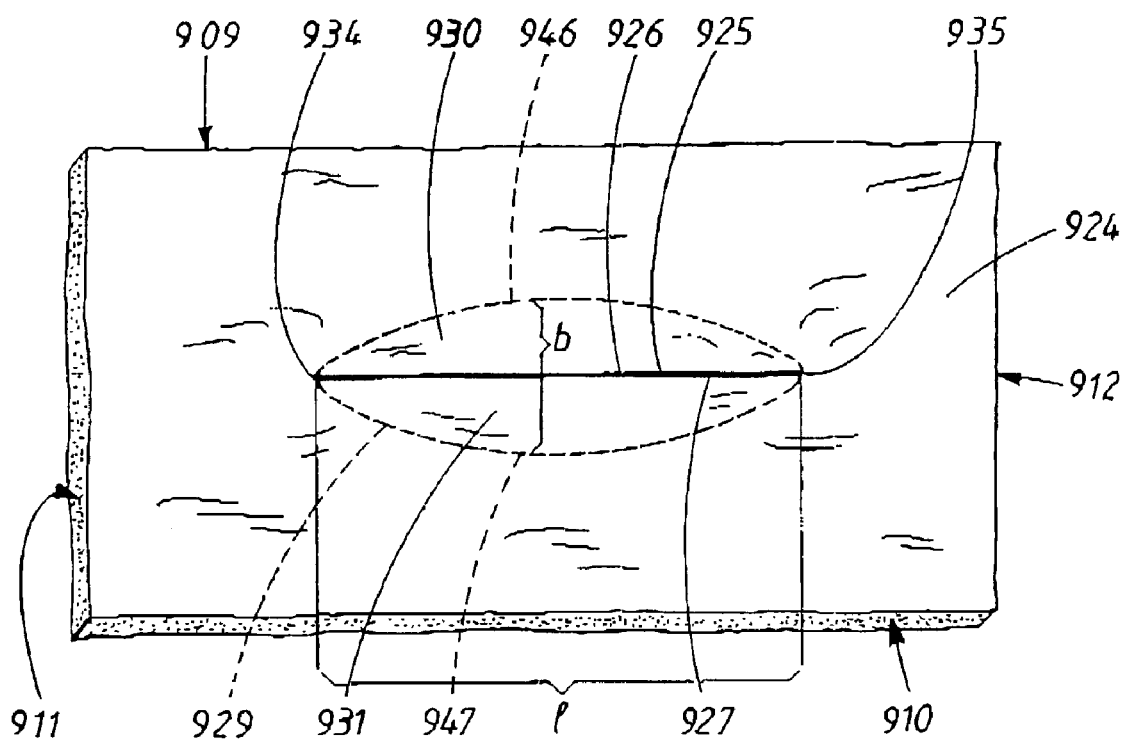
FIG. 9 shows an absorption layer for use in an absorption body according to the invention.
Figure 10:
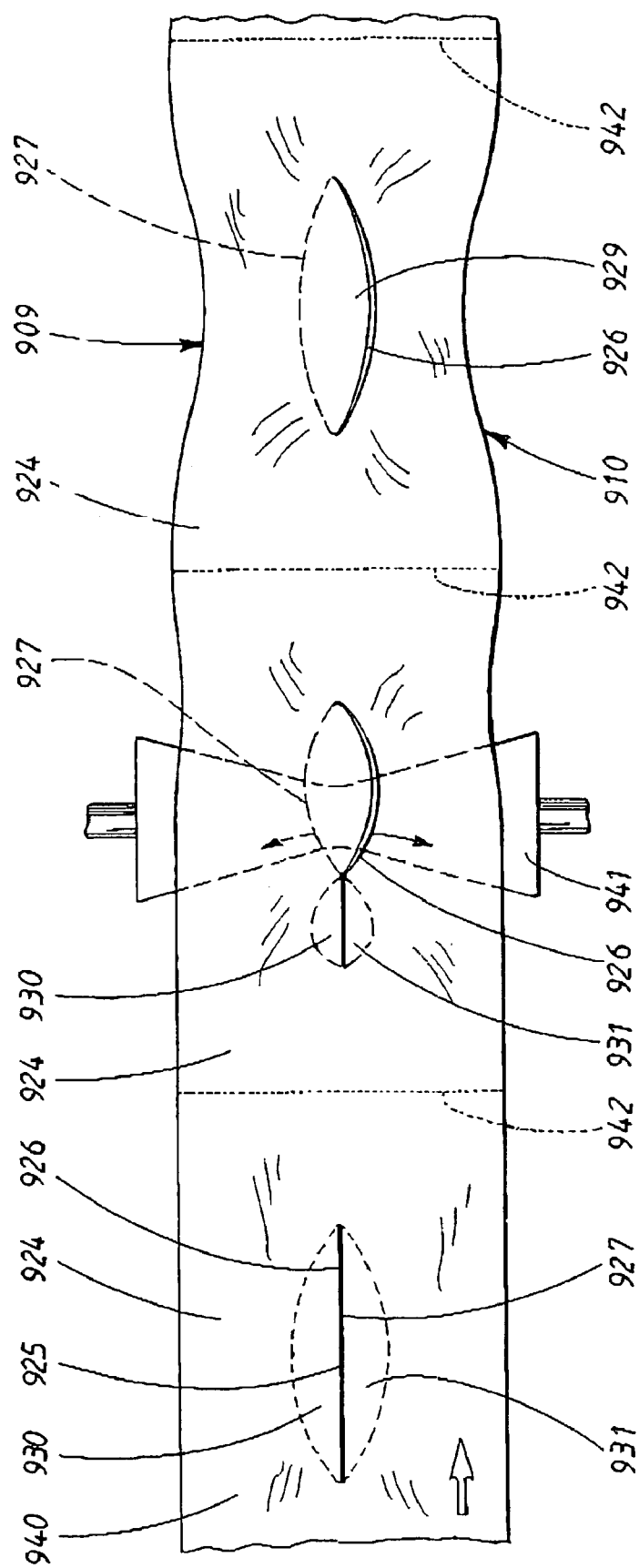
FIG. 10 shows a method to form an absorption layer according to the invention.
Figure 11:
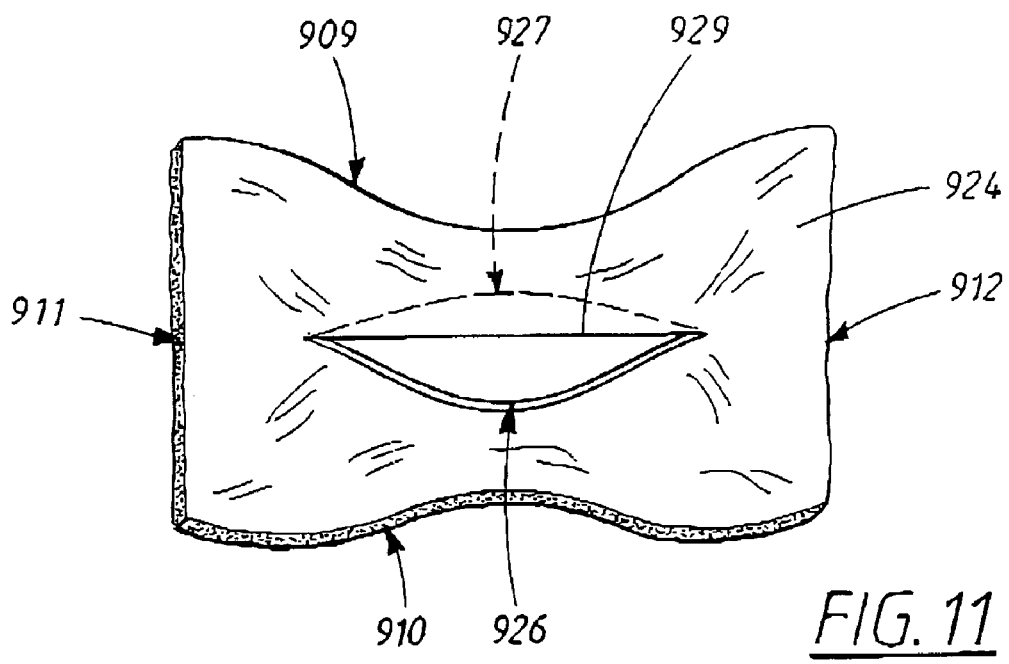
FIG. 11 shows a fully shaped absorption layer according to the invention.

In FIGS. 9–11 it is schematically shown how an absorption layer 924 according to the invention is slit and shaped. In FIG. 9 a rectangular, plane absorption layer 924 is shown with longitudinal side edges 909, 910 and transverse end edges 911, 912 and in which a straight penetrating slit 925 is arranged. The slit 925 is arranged parallel to the side edges 909, 910. On each side of the slit 925 the areas 930, 931 are indicated, areas that will be brought to overlap for shaping of the absorption layer 924. Each area 930, 931 is situated between a cut edge 926, 927 at the slit 925 and a curved demarcation line 946, 947, extending between the terminal points 934, 935 of the slit, is curved in a direction away from the slit 925.

The areas 930, 931 between the slit 925 and the demarcation lines 946, 947 together form an area with the shape of a boat, or a leaf, with two pointed tips 934, 935, a length, l, between the terminal points and a width, b.

Due to the demarcation lines 946, 947 being convexly curved between the terminal points 934, 935, the areas 930, 931 between the slit 925 and the demarcation lines 946, 947 have a greater width, b, at a distance from the terminal points 934, 935 than adjacent to the terminal points. The demarcation lines 946, 947 are preferably symmetrically arranged around the slit 925, in the longitudinal direction as well as in the transverse direction, as shown in the figures. However, it is possible to imagine demarcation lines with a different radius of curvature along different parts of the slit 925. For example, the radius of curvature can be larger close to one end 934 of the slit 925 than close to the other end 935.

In FIG. 10 a method for forming an overlapped area 929 along the slit 925 is shown. A plurality of coherent absorption layers 924 are fed as a continuous material web 940 over a rotating concave roll 941. In the figure it is shown how the cut edges 926, 927 are brought in opposite directions in over each other so that the areas 930, 931 on each side of the slit are brought to overlap. As a result of the overlapping, on the one hand a bunching of the absorption material within the overlapping area 929 is obtained and, on the other hand, the absorption layer 924 is shaped so that it has curved side edges 909, 910. Moreover, the absorption layer 924 is curved in the longitudinal direction as well as in the transverse direction.

The individual slit and shaped absorption layers 924 are separated from the running material web 940 along transverse dividing lines 942, which have been marked with dotted lines in FIG. 10.

In FIG. 11 it is shown how the fully shaped absorption layers 924 appear when separated from the material web 940 shown in FIG. 10. By means of the slitting and overlapping of the curved areas 930, 931 on each side of the slit 925, the absorption layers 924 have been given a curved shape in the longitudinal direction. In addition, the side edges 909, 910 of the absorption layer 924 have been curved inwards, in a direction towards the slit 925, so that the absorption layer 924 is almost hourglass-shaped in the plane.

It is usually expedient to fix the absorption layer 924 in the shaped state. Fixation can, for example, be accomplished through gluing, or welding, or through activation of a binding agent included in the absorption layer, for example thermoplastic fibres. Stabilization of the shape of the absorption layer 924 can also be accomplished through securing an additional material layer, for example through gluing or welding, to the folded-out absorption layer 924. Such an additional material layer can, for example, be a fluid-permeable cover layer or a fluid-impermeable cover layer, or a layer which acts, in a completed absorbent article, as a reinforcement layer, as a fluid-receiving layer, a fluid-dispersion layer, or another absorption layer. A stabilizing layer can be secured over the overlapped area in the absorption layer, on one or both sides thereof.

The absorption layer 924 may have another original shape than the rectangular shape shown, for example hourglass-shape or oval shape. As mentioned earlier, several slits 925 can be arranged in the same absorption layer 924. The slits can be arranged in different layers in relation to each other and may be placed with the overlapping portions 930, 931 completely or partially overlapping one another, or be separated in the plane. By arranging slits 925 in the end portions of an article, the end portions can also be shaped in a desired way. The slits have been shown to be centrally arranged in the longitudinal direction in the described embodiments, but can, if considered suitable, be located somewhat displaced towards an end portion, preferably towards that end portion that during use is intended to be directed forwards on the user, at least if the additional absorption capacity is intended for urine absorption.

The slit 925 can be made through one or both of the cover layers in an absorbent article. Furthermore, the absorption layer can comprise a fluid-transporting layer, and/or a fluid storage layer, which can be slit together with the absorption layer.

The shaping of an absorption layer according to the invention has been shown, in FIGS. 9–11, performed by a concave, rotating roll. Of course, it is alternatively possible to accomplish the shaping and the joining of different parts of an absorption layer by allowing the absorption layer to pass over a concave folding plate, or over two rotating conventional cylindrical rolls placed at an angle.

Figure 12:
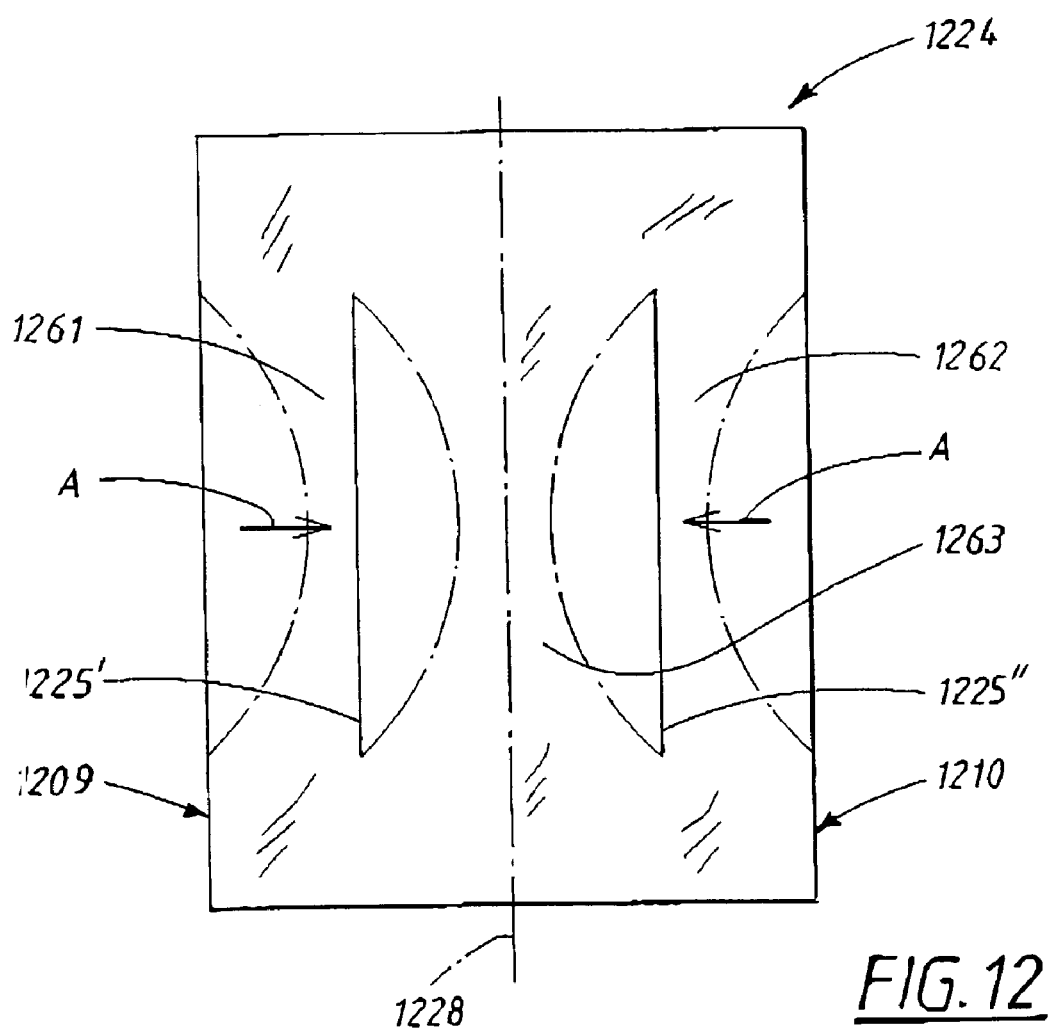
FIG. 12 shows an absorption layer according to an alternative embodiment of the invention.

In FIG. 12 an absorption layer 1224 with two slits 1225', 1225" is shown. The absorption layer 1224 has been brought over a concave, rotating roll, as a result of which a band-shaped area 1261, 1262 between each slit 1225', 1225" and a corresponding side edge 1209, 1210 on the absorption layer 1224 has been brought in the direction of the arrows A in towards the longitudinal centre line 1228 of the absorption layer 1224. Before the shaping, the absorption layer 1224 is rectangular, which is shown with continuous lines in the figure. After the shaping, the layer 1224 adopts the plan shape, implied with dashed-dotted lines. Thus, the absorption layer 1224 has, after the shaping, curved side edges 1209, 1210. The band-shaped areas 1261, 1262 may be brought in under the band-shaped area 1263 between the slits 1225', 1225", or be arranged above the central band-shaped area 1263. As the shaped absorption layer 1224 is arranged in an absorbent article, this can be done with the central band-shaped area 1263 closest to the fluid-permeable cover layer, or closest to the fluid-impermeable cover layer.

Figure 13:
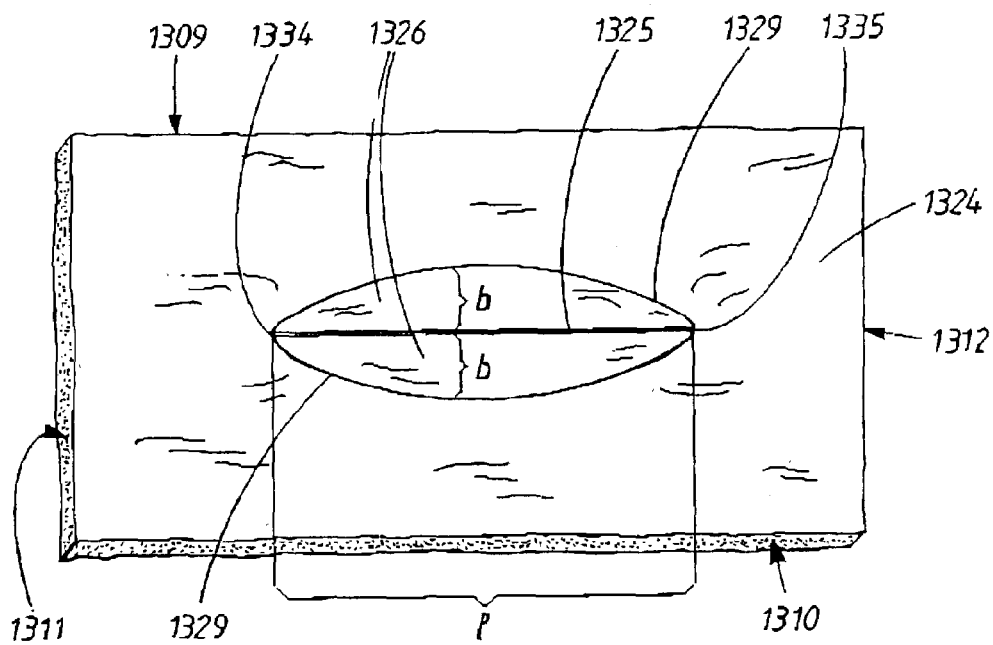
FIG. 13 shows a further absorption layer for use in an absorption body according to the invention.

FIGS. 13–16 show diagrammatically how an absorption layer 1324 according to the invention is slit and shaped. FIG. 13 shows a rectangular, plane absorption layer 1324 with longitudinal side edges 1309, 1310 and transverse end edges 1311, 1312, in which layer a penetrating slit 1325 is arranged. The slit 1325 is arranged parallel to the side edges 1309, 1310. On both sides of the slit 1325, curved fold indications in the form of compression lines 1329 curved in a direction away from the slit 1325 have been formed. The compression lines 1329 delimit a portion 1326 on each side of the slit 1325, which portion is located between the slit 1325 and the respective compression line 1329.

The portions 1326 between the slit 1325 and the compression lines 1329 together form an area which has the shape of a boat, or a leaf, with two pointed ends 1334, 1335, a length, l, between the terminal points and a width, b, on each portion 1326 between the slit 1325 and the respective compression line 1329.

By virtue of the compression lines 1329 being curved convexly between the ends 1334, 1335, the portions 1326 between the slit 1325 and the compression lines 1329 have a greater width, b, at a distance from the pointed ends 1334, 1335 than close to the ends. The compression lines 1329 are preferably arranged symmetrically around the slit 1325, in both the longitudinal direction and the transverse direction, as shown in the figures. However, it is conceivable to arrange compression lines 1329 with a different radius of curvature along different parts of the slit 1325. For example, the radius of curvature can be greater close to one end 1334 of the slit 1325 than close to the other end 1335. The compression lines 1329 do not have to be continuous either, but broken lines or spot compressions arranged along curved fold lines can alternatively be used as fold indications. It is of course also possible to use other types of fold indication, such as material weakenings and cuts, or perforations arranged along the fold lines.

Figure 14:
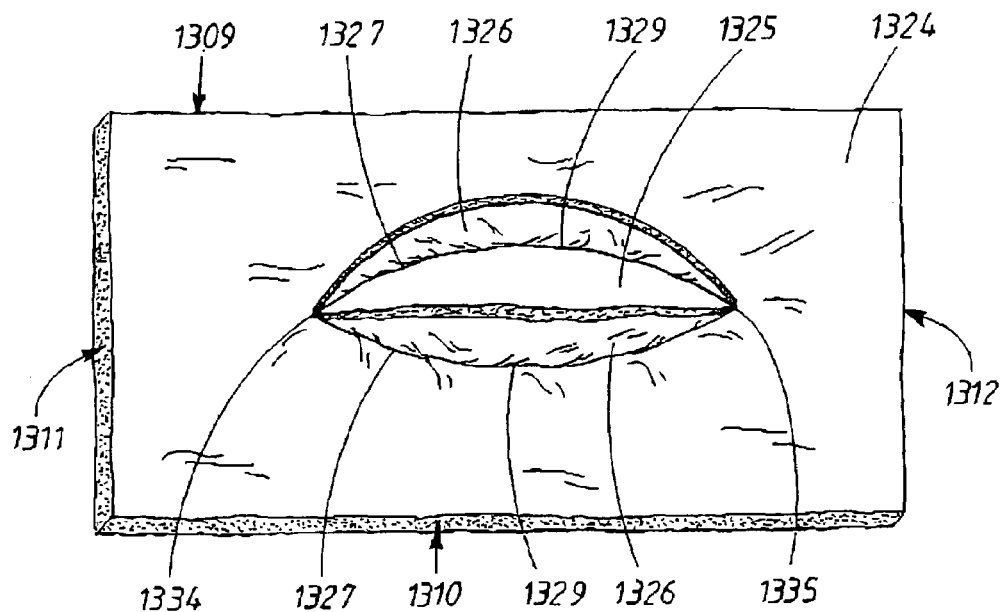
FIG. 14 shows the absorption layer in FIG. 13 as it appears after a first folding step.

FIG. 14 shows the absorption layer 1324 as it appears when the portions 1326 on both sides of the slit 1325 have been folded up out of the plane of the absorption layer 1324 along the compression lines 1329. The folding-up of the portions 1326 can be carried out by, for example, the absorption layer 1324 being made to pass over a rotating roll with an upwardly projecting part which folds the portions 1326 at the side of the slit 1325 straight up from the compression lines 1329.

The folded-up portions 1326 are subsequently folded down towards the plane of the absorption layer 1324, for example by means of a plough-shaped folding plate. For certain embodiments of the invention, the folding-down operation can be omitted. For example, the folded-up portions 1326 can, after the curved fold edges 1327 have been brought together, together form a narrow raised portion, what is known as a hump, on a sanitary napkin or the like.

Figure 15:
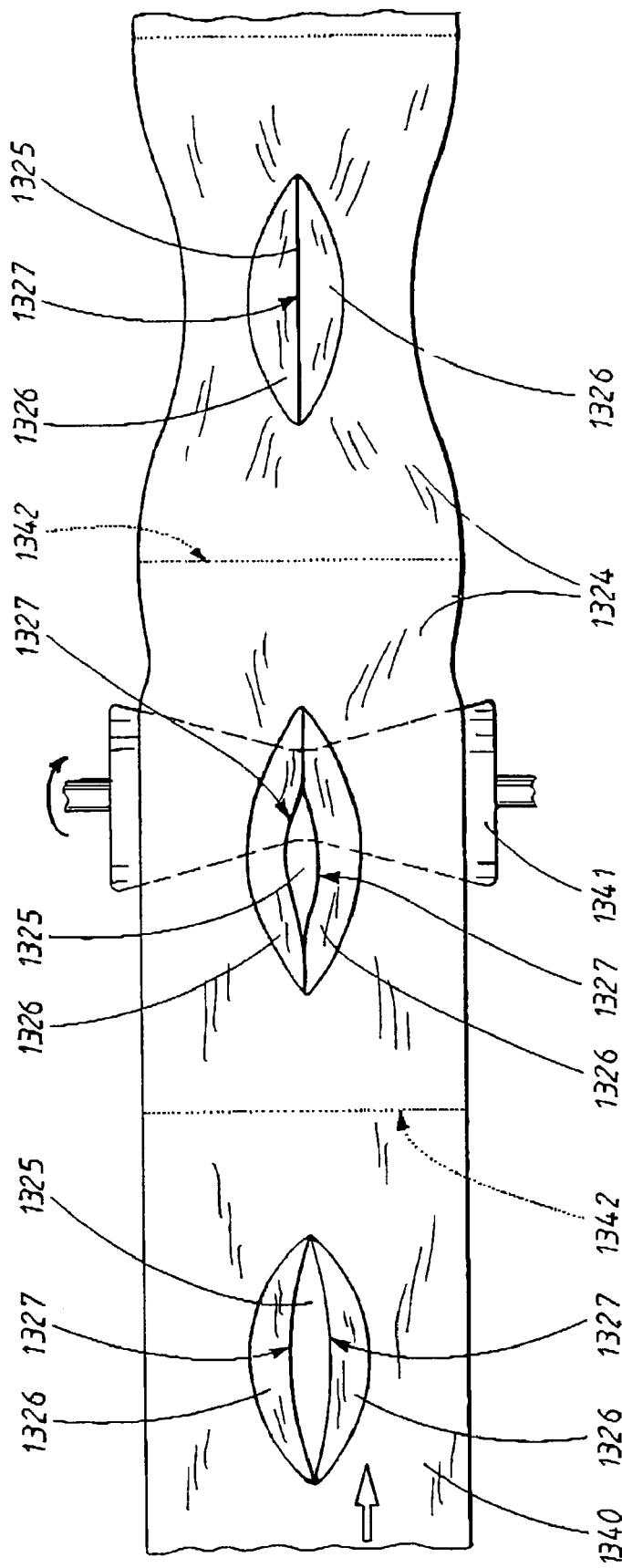
FIG. 15 shows a method of shaping an absorption layer of the kind shown in FIGS. 13 and 14.

FIG. 15 shows a method of bringing together the curved fold edges 1327 formed at the compression lines 1329. A plurality of connected absorption layers 1324 are fed as a continuous material web 1340 over a rotating concave roll 1341. The figure shows how the fold edges 1327 are brought together completely. Alternatively, a small clearance, up to roughly 20 mm, can be left between the fold edges 1327.

The individual slit and shaped absorption layers 1324 are separated from the running material web 1340 along transverse dividing lines 1342, which have been marked by dotted lines in FIG. 15.

Figure 16:
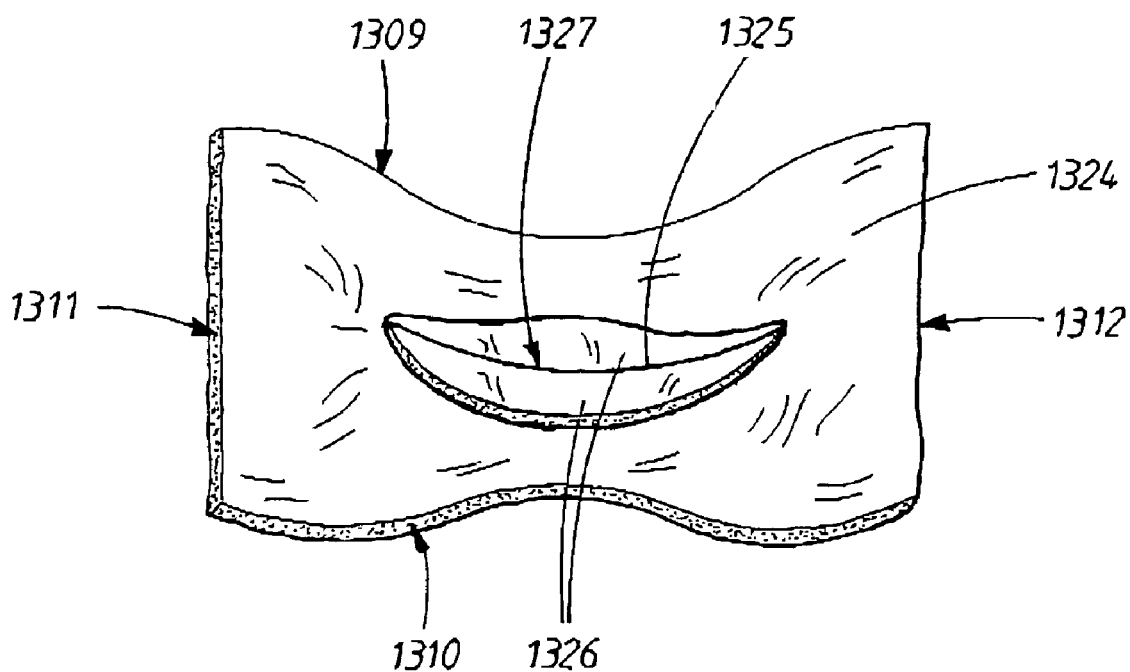
FIG. 16 shows a fully shaped absorption layer of the kind shown in FIGS. 13 and 14.

FIG. 16 shows how the fully shaped absorption layers 1324 appear when they have been separated from the material web 1340 shown in FIG. 15. The absorption layers 1324 have, by cutting, folding and bringing together the curved fold edges 1327, been given a curved shape in the longitudinal direction. Moreover, the side edges 1309, 1310 of the absorption layer 1324 have been curved inwards, in a direction towards the slit 1325, so that the absorption layer 1324 is almost hourglass-shaped in the plane.

It is usually suitable to fix the absorption layer 1324 in the shaped state, with the portions 1326 located on either side of the slit 1325 folded down towards the absorption layer 1324. The fixation can be brought about by, for example, gluing or welding, or by activating a binding agent included in the absorption layer, for example thermoplastic fibres.

Stabilization of the shape of the absorption layer 1324 can also be accomplished through securing an additional material layer, for example through gluing or welding, to the folded-out absorption layer 1324. Such an additional material layer can be, for example, a fluid-permeable cover layer or a fluid-impermeable cover layer, or a layer which acts, in a completed absorbent article, as a reinforcement layer, as a fluid-receiving layer, a fluid-dispersion layer, or another absorption layer. A stabilizing layer can be secured either over the slit 1325 in the absorption layer, on the same side as the folded-out portions 1326, and/or on the opposite side.

The absorption layer 1324 may have another original shape than the rectangular shape shown, for example hourglass-shape or oval shape. As mentioned earlier, several slits 1325 can be arranged in the same absorption layer 1324. The slits can be arranged in different layers in relation to each other and may be placed with the folded-out parts 1326 completely or partially overlapping one another, or be separated in the plane. By arranging slits 1325 in the end portions of an article, these can also be shaped in a desired way. The slits have been shown to be centrally arranged in the described embodiments, but can, if considered suitable, be located somewhat displaced towards an end portion, preferably towards that end portion that during use is intended to be directed forwards on the user, at least if the additional absorption capacity is intended for urine absorption.

The slit 1325 can be made through one or both of the cover layers in an absorbent article.

Figure 17:
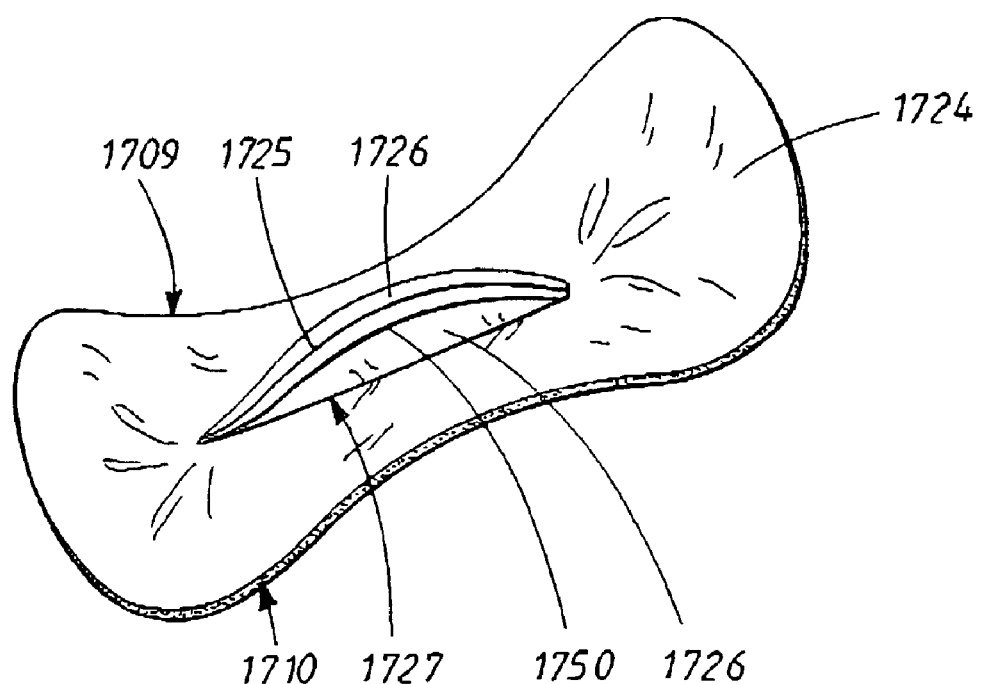
FIG. 17 shows an absorption layer with a raised portion.

FIG. 17 shows an absorption layer 1724 which is suitable for, for example, use in a sanitary napkin or the like. The absorption layer 1724 is provided with a longitudinal slit 1725 and, as described earlier, has folded-up, segment-shaped portions 1726 on both sides of the slit. By bringing the fold edges 1727 of the folded portions 1726 together, the absorption layer 1724 has been given a curved shape in the longitudinal direction, with curved side edges 1709, 1710. Furthermore, the folded portions 1726 are not folded down towards the plane of the absorption layer 1724 but have been joined together in a state in which they are raised essentially at right angles from the plane of the absorption layer. In this way, the folded portions 1726 form a narrow, arched raised portion 1750 which can advantageously be arranged so that it faces the user's body during use of an article comprising the absorption layer 1724. Such body-following raised portions are advantageous, as they facilitate correct positioning of the absorbent article in relation to the user's body and as they can moreover catch and absorb discharged body fluid as soon as it leaves the user's body.

Figure 18:
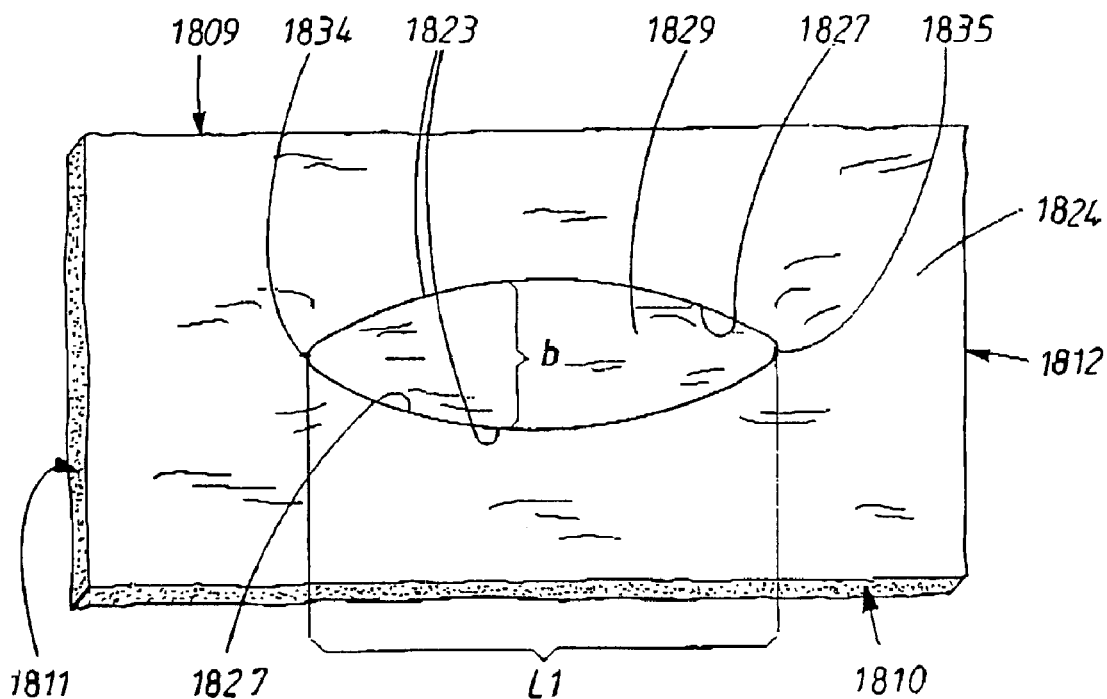
FIG. 18 shows a further absorption layer for use in an absorption body according to the invention.
Figure 19:
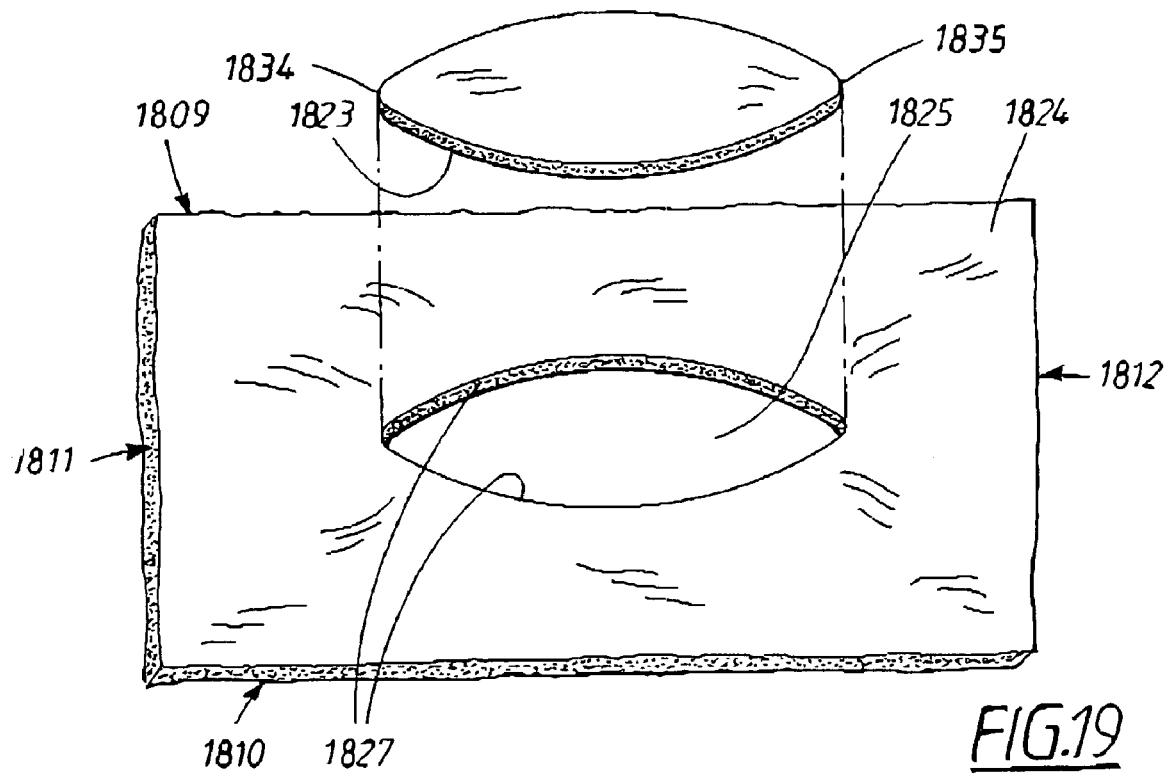
FIG. 19 shows the absorption layer in FIG. 18 as it appears after removal of a cutout part.

FIGS. 18–23 show diagrammatically how an absorption layer 1824 according to the invention is opened and shaped. FIGS. 18 and 19 show a rectangular, plane absorption layer 1824 with longitudinal side edges 1809, 1810 and transverse end edges 1811, 1812, in which layer a penetrating opening 1825 is arranged. The opening 1825 is arranged parallel to the side edges 1809, 1810, and in FIG. 18 the opening is shown with the part, the cutout part 1829, which is to be removed still in the opening 1825. The opening is delimited by surrounding cut edges 1827.

The cutout part 1829 has the shape of a boat or a leaf with two pointed ends with terminal points 1834, 1835 and a length, L1, between the terminal points 1834, 1835, and is delimited by surrounding free edges 1823.

By virtue of the free edges 1823 being curved convexly between the ends 1834, 1835, overlapping areas 1826 (FIG. 21) between the cut edges 1827 and the free edges 1823 have a greater width at a distance from the pointed ends 1834, 1835 than close to the ends. The cut edges 1827 are preferably arranged symmetrically around the opening 1825, or around a fluid-admission channel 1830 formed after the cut edges 1827 have been brought together, in both the longitudinal direction and the transverse direction, as shown in the figures. However, it is conceivable to arrange the cut edges 1827 with a different radius of curvature along different parts of the opening 1825. For example, the radius of curvature can be greater at one end of the opening 1825 than at the other end.

FIG. 19 shows the absorption layer 1824 as it appears when the cutout part 1829 has been removed from the absorption layer 1824, which can take place in a number of ways known within the technical field.

FIG. 20 shows a method of bringing the cut edges 1827 together to form the fluid-admission channel 1830. A plurality of connected absorption layers 1824 are fed as a continuous material web 1840 over a rotating concave roll 1841.

The figure shows how the cut edges 1827 are brought together and form a narrow fluid-admission channel 1830. Bringing the cut edges 1827 together over the roll 1841 also deforms the absorption layer 1824 in three dimensions in such a way as has been described above. FIG. 20 shows that the absorption layer 1824 has, during and after rolling, been deformed into an hourglass shape in the plane. It is of course possible to bring the cut edges 1827 together completely, three-dimensional shaping of the absorption layer 1824 then being brought about, but not the formation of an admission channel.

The individual shaped absorption layers 1824 with fluid-admission channel 1830 are separated from the running material web 1840 along transverse dividing lines 1842, which have been marked by dotted lines in FIG. 20.

FIG. 21 shows another embodiment of the invention, where the cutout part 1829 is applied to the top side of the absorption layer 1824, over the fluid-admission channel 1830, in connection with the absorption layer 1824 being moved over the roll 1841. The figure shows that the cutout part is applied to the absorption layer, over the fluid-admission channel 1830 formed, in a continuous movement which coincides with the cut edges 1827 being brought together over the roll until the fluid-admission channel 1830 has a predetermined width. The cutout part can be used to lock the cut edges in a predetermined position. The locking can be effected by gluing, heating, welding or another method suitable for the purpose. It can also be possible for the cutout part to be applied to the absorption layer from the roll side.

In another embodiment of the application of the cutout part described above (not shown), the cutout part 1829 is applied to the underside of the absorption layer 1824, over the fluid-admission channel 1830, after rolling, when the whole fluid-admission channel has already been formed in a predetermined size, which is shown in FIG. 20.

Figure 22:
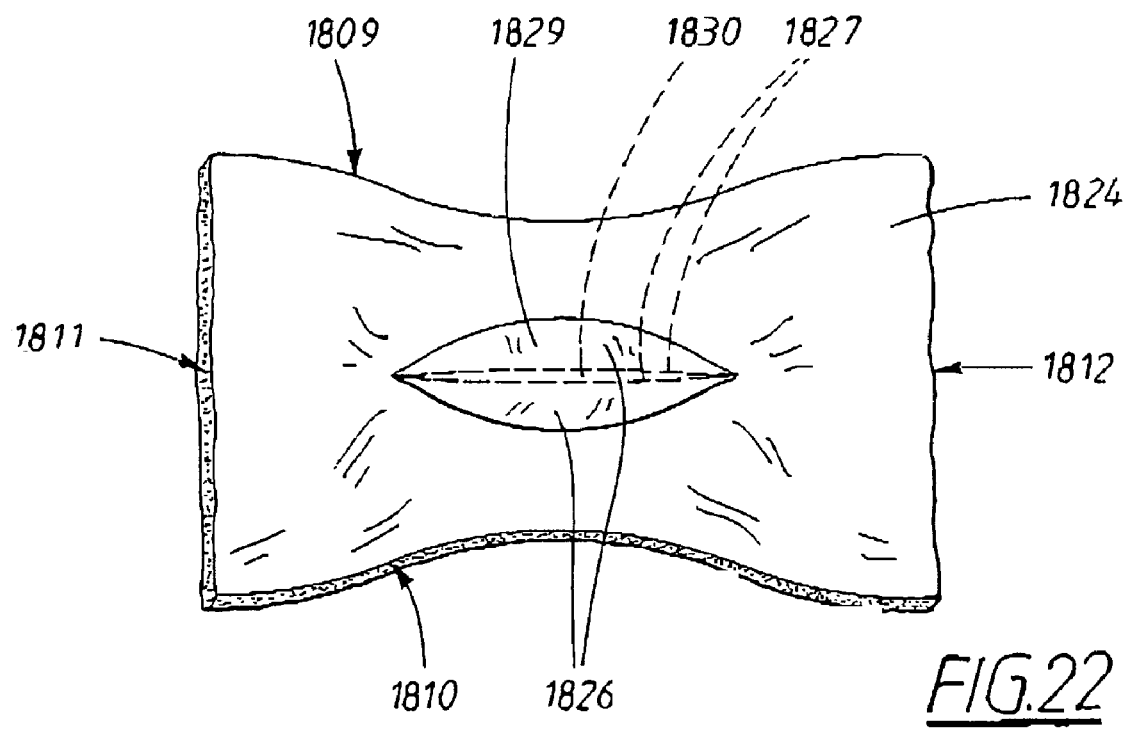
FIG. 22 shows an absorption layer shaped according to the method in FIG. 7 or 8, with application of a cutout part.

FIG. 22 shows how the fully shaped absorption layers 1824 appear when they have been separated from the material web 1840 shown in FIG. 20 or 21. The absorption layers 1824 have, by virtue of the cut edges 1827 being brought together, been given a curved shape in the longitudinal direction. Moreover, the side edges 1809, 1810 of the absorption layer 1824 have been curved inwards, in a direction towards the fluid-admission channel 1830, so that the absorption layer 1824 is almost hourglass-shaped in the plane.

It is usually suitable to fix the absorption layer 1824 in the shaped state, with the overlapping portions 1826, of the cutout part 1829, located on either side of the fluid-admission channel 1830 against the absorption layer 1824. The fixation can be brought about by, for example, gluing or welding, or by activating a binding agent included in the absorption layer, for example thermoplastic fibres. Stabilization of the shape of the absorption layer 1824 can also be accomplished through securing an additional material layer, for example through gluing or welding, to the absorption layer 1824. Such an additional material layer can be, for example, a fluid-permeable cover layer or a fluid-impermeable cover layer, or a layer which acts, in a completed absorbent article, as a reinforcement layer, as a fluid-receiving layer, a fluid-dispersion layer, or another absorption layer. A stabilizing layer can be secured either over the fluid-admission channel 1830 in the absorption layer, on the same side as the cutout part 1829, and/or on the opposite side.

The shaping of an absorption layer according to the invention has been shown, in FIGS. 20–22, performed by a concave, rotating roll. Of course, it is alternatively possible to accomplish the shaping and the bringing together of the cut edges to form a fluid-admission channel in the absorption layer by allowing the absorption layer to pass over a concave folding plate, or over two rotating conventional cylindrical rolls placed at an angle.

The absorption layer 1824 may have another shape of origin than the rectangular shape shown, for example hourglass-shape or oval shape. Several openings can be arranged in the same absorption layer 1824. The openings can be arranged in different layers in relation to each other, and the cutout parts 1829 may be placed completely or partially overlapping one another, or be separated in the plane. By arranging openings in the end portions of an article, these can also be shaped in a desired way in accordance with the invention.

Openings have been shown to be centrally arranged in the described embodiments, but can, if considered suitable, be located somewhat displaced towards an end portion, preferably towards that end portion that during use is intended to be directed forwards on the user, at least if the additional absorption capacity obtained by application of the cutout part is intended for urine absorption.

Openings can be made through one or both cover layers of an absorbent article.

Figure 23:
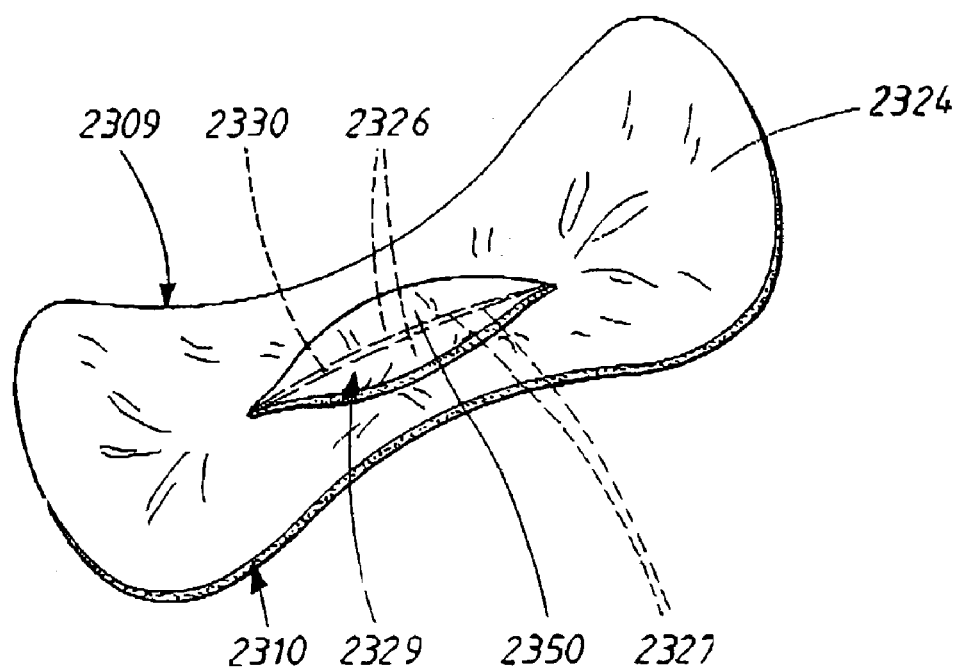
FIG. 23 shows a fully shaped absorption layer with application of a cutout part.

FIG. 23 shows an absorption layer 2324 which is suitable for, for example, use in a sanitary napkin or the like. The absorption layer 2324 is provided with a longitudinal fluid-admission channel 2330 and, as described earlier, has the cutout part 2329 with the overlapping parts 2326 on both sides of the fluid-admission channel 2330. By bringing the cut edges 2327 together, the absorption layer 2324 has been given a curved shape in the longitudinal direction, with curved side edges 2309, 2310. The applied cutout part 2329 forms a narrow, arched raised portion 2350 which can advantageously be arranged so that it faces the user's body during use of an article comprising the absorption layer 2324. Such body-following raised portions are advantageous, as they facilitate correct positioning of the absorbent article in relation to the user's body and as they can moreover catch and absorb discharged body fluid as soon as it leaves the user's body. The cutout part can also be applied to the other side of the absorption layer in accordance with what was shown in FIG. 4*c*.

The incontinence shield 301, shown in FIGS. 3 and 4, and the sanitary napkin 701 in FIGS. 7 and 8, may be supplied with elastic members. Such elastic members contribute to curving and shaping of the absorbent article and can also be used to create raised barriers along the side edges of the article. As the invention makes it possible to accomplish an absorbent article with a shape that is anatomically correct, it is, however, generally not necessary to use elastic members.

What is claimed is:

1. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the absorption body comprises a unitary structure, wherein the absorption layer is fixed in a predetermined shape by a stabilizing means, and wherein the stabilizing means is a binding agent, which is part of the absorption layer.

2. An absorbent article according to claim 1, wherein the two cut edges are arcuate and are moved towards one another in such a manner that the two cut edges run essentially parallel in the longitudinal direction of the article, as a result of which the absorption layer is deformed into an hourglass shape in the plane and curved in space.

3. An absorbent article according to claim 1, wherein the movement is carried out in such a manner that a first area located along the first cut edge overlaps a second area located along the second cut edge, the overlapping areas having at least one arcuate curved edge.

4. An absorbent article according to claim 3, wherein the absorption layer exhibits at least a second slit, which is essentially parallel to the first slit and wherein each slit exhibits a first cut edge and a second cut edge, which are displaced in pairs in relation to each other in such a manner that the absorption layer exhibits at least one overlapping area along each slit, wherein the overlapping areas along each slit have an arcuate curved edge.

5. An absorbent article according to claim 1, wherein the cut edges, before movement, are arcuate and delimit an opening, formed by the slit, in the absorption layer.

6. An absorbent article according to claim 1, wherein the article exhibits two end portions, and a crotch portion situated between the end portions, which crotch portion has a lesser extension in the transverse direction than the end portions, and wherein the slit is arranged at least principally in the crotch portion.

7. An absorbent article according to claim 1, wherein the slit extends in the longitudinal direction of the article.

8. An absorbent article according to claim 1, wherein the cut edges are displaced in relation to one another and wherein the mutually displaced cut edges are situated at a greatest distance of 0–20 mm from each other.

9. An absorbent article according to claim 1, wherein the binding agent consists of thermoplastic fibres.

10. An absorbent article according to claim 1, wherein the article is a diaper for children and the slit has a length between the terminal points of 15–40 centimetres.

11. An absorbent article according to claim 1, wherein the article is a diaper for adults and the slit has a length between the terminal points of 20–60 centimetres.

12. An absorbent article according to claim 1, wherein the article is a sanitary napkin or an incontinence shield and the slit has a length between the terminal points of 10–40 centimetres.

13. An absorbent article according to claim 1, wherein the absorption layer is formed from an essentially plane, rectangular blank.

14. An absorbent article according to claim 1, wherein the penetrating slit is formed at a predetermined distance from outer edges of the absorption layer.

15. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the movement is carried out in such a manner that a first area located along the first cut edge overlaps a second area located along the second cut edge, the overlapping areas having at least one arcuate curved edge, wherein the absorption layer exhibits at least a second slit, which is essentially parallel to the first slit and wherein each slit exhibits a first cut edge and a second cut edge, which are displaced in pairs in relation to each other in such a manner that the absorption layer exhibits at least one overlapping area along each slit, wherein the overlapping areas along each slit have an arcuate curved edge, wherein the overlapping areas form an area with three overlapping layers of the absorption layer.

16. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the movement is carried out in such a manner that a first area located along the first cut edge overlaps a second area located along the second cut edge, the overlapping areas having at least one arcuate curved edge, wherein the overlapping areas are affixed to each other.

17. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the cut edges, before movement, are arcuate and delimit an opening, formed by the slit, in the absorption layer, wherein a cutout part removed from the absorption layer is applied to the absorption layer with those parts of the cutout part which lie against the absorption layer constituting overlapping parts.

18. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the absorption layer is fixed in a predetermined shape by a stabilizing means, wherein the stabilizing means is a stabilizing layer, which is firmly attached to the absorption layer, wherein the stabilizing layer constitutes a distance layer between the absorption body and the fluid-permeable surface of the cover.

19. An absorbent article according to claim 18, wherein the distance layer is a porous fluid-receiving layer.

20. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the absorption body comprises a unitary structure, wherein the absorption layer is fixed in a predetermined shape by a stabilizing means, and wherein the stabilizing means is a glue.

21. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the absorption layer is fixed in a predetermined shape by a stabilizing means, wherein the stabilizing means comprises a mechanical fastening between overlapping areas in the absorption layer.

22. An absorbent article according to claim 21, wherein the article comprises a fluid-permeable cover layer and a fluid-impermeable cover layer and wherein the slit extends through the fluid-permeable cover layer.

23. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the slit also extends through the cover of the article.

24. An absorbent article with a longitudinal direction and a transverse direction and comprising an absorption body enclosed in a cover, wherein the cover has a fluid-permeable surface and a fluid-impermeable surface and wherein the absorption body comprises at least one absorption layer exhibiting a penetrating slit with a first cut edge and a second cut edge, wherein the absorption layer is shaped by the material on both sides of the two cut edges being moved in a direction essentially at right angles to the slit and being locked in a moved position, wherein the absorption body comprises a unitary structure, wherein the absorption layer is a layer of cellulose fluff pulp with a density of 0.2–1.0 g/cm$^3$.

25. An absorbent article according to claim 24, wherein the stabilizing means is a stabilizing layer, which is firmly attached to the absorption layer.

* * * * *